(12) United States Patent
Ghosh

(10) Patent No.: US 9,359,317 B2
(45) Date of Patent: Jun. 7, 2016

(54) SMALL MOLECULE INHIBITORS OF HIV PROTEASES

(71) Applicant: Arun K. Ghosh, West Lafayette, IN (US)

(72) Inventor: Arun K. Ghosh, West Lafayette, IN (US)

(73) Assignee: Purdue Research Foundation, West Lafayette, IN (US)

(*) Notice: Subject to any disclaimer, the term of this patent is extended or adjusted under 35 U.S.C. 154(b) by 22 days.

(21) Appl. No.: 14/157,042

(22) Filed: Jan. 16, 2014

(65) Prior Publication Data

US 2014/0135321 A1 May 15, 2014

Related U.S. Application Data

(62) Division of application No. 12/812,908, filed as application No. PCT/US2009/031183 on Jan. 16, 2009, now abandoned.

(60) Provisional application No. 61/083,744, filed on Jul. 25, 2008, provisional application No. 61/021,702, filed on Jan. 17, 2008.

(51) Int. Cl.
A61K 31/34 (2006.01)
C07D 307/16 (2006.01)
A61K 31/341 (2006.01)
C07D 493/04 (2006.01)
C07D 207/48 (2006.01)
C07D 493/08 (2006.01)
C07D 493/18 (2006.01)

(52) U.S. Cl.
CPC ............ C07D 307/16 (2013.01); A61K 31/341 (2013.01); C07D 207/48 (2013.01); C07D 493/04 (2013.01); C07D 493/08 (2013.01); C07D 493/18 (2013.01)

(58) Field of Classification Search
CPC .................................................. A61K 31/341
USPC ........................................................ 514/471
See application file for complete search history.

(56) References Cited

U.S. PATENT DOCUMENTS

| | | | |
|---|---|---|---|
| 5,723,490 A | 3/1998 | Tung et al. | |
| 5,728,718 A | 3/1998 | Randad et al. | |
| 6,313,345 B1 | 11/2001 | Vazquez et al. | |
| 6,649,651 B1 | 11/2003 | Wigerinck et al. | |
| 2004/0122000 A1 | 6/2004 | Hale et al. | |
| 2005/0159469 A1 | 7/2005 | Randolph et al. | |
| 2005/0214890 A1 | 9/2005 | Tan et al. | |
| 2006/0293286 A1 | 12/2006 | Erickson et al. | |
| 2007/0082883 A1 | 4/2007 | Ghosh et al. | |
| 2007/0117793 A1 | 5/2007 | Ghosh et al. | |
| 2008/0096942 A1 | 4/2008 | Tenbrink et al. | |
| 2010/0113582 A1 | 5/2010 | Ghosh | |
| 2011/0046199 A1 | 2/2011 | Ghosh | |

FOREIGN PATENT DOCUMENTS

| | | |
|---|---|---|
| EP | 0984000 | 3/2000 |
| EP | 1516872 | 3/2005 |
| EP | 1577299 | 9/2005 |
| WO | WO 96/22087 | 7/1996 |
| WO | WO 96/33187 | 10/1996 |
| WO | WO 99/67254 | 12/1999 |
| WO | WO 01/25240 | 4/2001 |
| WO | WO 2008/133734 | 11/2008 |
| WO | WO-2009/091941 A1 | 7/2009 |
| WO | WO 2010/002994 | 1/2010 |
| WO | WO 2010/006050 | 1/2010 |

OTHER PUBLICATIONS

Supplementary European Search Report for European Patent Application No. 09702571 dated Jan. 8, 2014, 4 pages.
Ghosh, et al. "TiCl₄ Promoted Multi-component Reaction: A New Entry to the Functionalized α-Amino Acids," Organic Letters, vol. 7, 2005, pp. 7-10.
Hideki Moriyama et al: "Azasugar-Based MMP/ADAM Inhibitors as Antipsoriatic Agents", Journal of Medicinal Chemistry, vol. 47, No. 8, Apr. 1, 2004, pp. 1930-1938.
Hideki Moriyama et al: "Structure-activity relationships of azasugar-based MMP/ADAM inhibitors", Bioorganic & Medicinal Chemistry Letters, vol. 13, No. 16, Aug. 1, 2003, pp. 2737-2740.
Sureshkumar D et al: "Synthesis of enantiopure bis-aziridines, bis-epoxides, and aziridino-epoxides from d-mannitol", Tetrahedron, Elsevier Science Publishers, Amsterdam, NL, vol. 62, No. 43, Oct. 23, 2006, pp. 10162-10170.
Joly G J et al: "Use of the N-tosyl-activated aziridine 1,2-dideoxy-1,2-iminomannitol as a synthon for 1-deoxymannojirimycin analogues", Tetrahedron Letters, Pergamon, GB, vol. 41, No. 13, Mar. 1, 2000, pp. 2223-2226.
Jackson R F W et al: "A new approach to the synthesis of beta-hydroxy-alpha-amino acids using (arylthio)nitrooxiranes", The Journal of Organic Chemistry, American Chemical Society [NOT]Etc. , US, vol. 60, Jan. 1, 1995, pp. 6431-6440.
Hun Park K et al: "Efficient cleavage of terminal acetonide group: Chirospecific synthesis of 2,5-dideoxy-2,5-imino-D-mannitol", Tetrahedron Letters, Pergamon, GB, vol. 35, No. 52, Dec. 26, 1994, pp. 9737-9740.
Amano et al., "A Novel Bis-Tetrahydrofuranylurethane-containing Nonpeptidic Protease Inhibitor (PI), GRL-98065, is Potent against Multiple-PI-Resistant Human Immunodeficiency Virus in vitro," Antimicrobial Agents and Chemotherapy, vol. 51, No. 6, 2143-2155 (2007).
Ami et al., "Synthesis of Novel Amino Acids, L-Bis-Tetrahydrofuranylglycines," Tetrahedron Letters, vol. 43, 2931-2934 (2002).

(Continued)

Primary Examiner — Shengjun Wang
(74) Attorney, Agent, or Firm — Schwegman Lundberg & Woessner, P.A.

(57) ABSTRACT

Described herein are compounds, compositions, and methods for treating HIV and related diseases.

7 Claims, No Drawings

(56) References Cited

OTHER PUBLICATIONS

Babe et al., "Synthetic "interface" Peptides Alter Dimeric Assembly of the HIV 1 and 2 Proteases," Protein Science, vol. 1, No. 10, 1244-1253 (1992).
Bannwarth et al., "Molecular Tongs Containing Amino Acid Mimetic Fragments: New Inhibitors of Wild-Type and Mutated HIV-1 Protease Dimerization," J. Med. Chem., vol. 49, No. 15, 4657-4664 (2006).
Bastiaens et al., "Imaging the Intracellular Trafficking and State of the $AB_5$ Quaternary Structure of Cholera Toxin," EMBO Journal, vol. 15, No. 16, 4246-4253 (1996).
Bowman et al., "Switching between Allosteric and Dimerization Inhibition of HIV-1 Protease," Chemistry & Biology, vol. 12, No. 4, 439-444 (2005).
Carr, "Toxicity of antiretroviral therapy and implications for drug development," Nature Reviews Drug Disc, vol. 2, 624-634 (2003).
Chen et al., "Syntheses of a New Cerebroside Isolated from Typhonium Giganteum Engl," Chinese Journal of Chemistry, vol. 21, 937-943 (2003).
Davis et al., "Inhibition of HIV-1 Replication by a Peptide Dimerization Inhibitor of HIV-1 Protease", Antiviral Research, vol. 72, No. 2, 89-99 (2006).
De Clercq, "Strategies in the design of antiviral drugs," Nature Reviews Drug Disc, vol. 1, 13-25 (2002).
De Meyer et al., "TMC114, a Novel Human Immunodeficiency Virus Type 1 Protease Inhibitor Active against Protease Inhibitor-Resistant Viruses, Including a Broad Range of Clinical Isolates," Antimicrobial Agents and Chemotherapy, vol. 49, No. 6, 2314-2321 (2005).
Fang et al., "PCR-Mediated Recombination: A General Method Applied to Construct Chimeric Infectious Molecular Clones of Plasma-Derived HIV-1 RNA," Nature Medicine, vol. 5, No. 2, 239-242 (1999).
Firulli et al., "Altered Twist1 and Hand2 Dimerization is Associated with Saethre-Chotzen Syndrome and Limb Abnormalities," Nature genetics, vol. 37, No. 4, 373-381 (2005).
Friesner et al., "Glide: a new approach for rapid, accurate docking and scoring. 1. Method and assessment of docking accuracy," J. Med. Chem., vol. 47, 1739-1749 (2004).
Frutos et al., "Disruption of the HIV-1 Protease Dimer with Interface Peptides: Structural Studies Using NMR Spectroscopy Combined with [2-$^{13}$C]-Trp Selective Labeling," Peptide Science, vol. 88, 164-173 (2007).
Fumero et al., "New patterns of HIV-1 resistance during HAART," European Society of Clinical Microbiology and Infectious Diseases, vol. 9, 1077-1084 (2003).
Gatanaga et al., "Amino Acid Substitutions in Gag Protein and Non-Cleavage Sites are Indispensable for the Development of a High Multitude of HIV-1 Resistance Against Protease Inhibitors," Journal of Biological Chemistry, vol. 277, No. 8, 5952-5961 (2002).
Ghosh et al., "Potent HIV protease inhibitors incorporating high-affinity P2-ligands and (R)-(hydroxyethylamino)sulfonamide isostere," Bioorganic & Medicinal Chemistry Letters, vol. 8, 687-690 (1998).
Ghosh et al., "Structure based design: novel spirocyclic ethers as nonpeptidal P2-ligands for HIV protease inhibitors," Bioorganic & Medicinal Chemistry Letters, vol. 8, 979-982 (1998).
Ghosh et al., "Design and synthesis of novel HIV-1 protease inhibitors incorporating oxyindoles as the P'2-ligands," Bioorganic & Medicinal Chemistry Letters, vol. 16, 1869-1873 (2006).
Ghosh et al., "Structure-Based Design of Novel HIV-1 Protease Inhibitors to Combat Drug Resistance," J. Med. Chem., vol. 49, 5252-5261 (2006).
Ghosh et al., "Nonpeptidal P2 Ligands for HIV Protease Inhibitors: Structure-Based Design, Synthesis, and Biological Evaluation," J. Med. Chem., vol. 39, 3278-3290 (1996).
Grabar et al., "HIV infection in older patients in the HAART era," Journal of Antimicrobial Chemotherapy, vol. 57, 4-7 (2005).
Hirsch et al., "Immune reconstitution in HIV-infected patients," Clinical Infectious Diseases, 2004, 38:1159-66.
Hong et al., "Crystal structure of an in vivo HIV-1 protease mutant in complex with saquinavir: insights into the mechanisms of drug resistance," Protein Science, vol. 9, 1898-1904 (2000).
Ishima et al., "Solution Structure of the Mature HIV-1 Protease Monomer," J. Biol. Chem., vol. 278, No. 44, 43311-43319 (2003).
Ishima et al., "Folded Monomer of HIV-1 Protease," J. Biol. Chem., vol. 276, No. 52, 49110-49116 (2001).
Kaplan et al., "Selection of multiple human immunodeficiency virus type 1 variants that encode viral proteases with decreased sensitivity to an inhibitor of the viral protease," PNAS USA, vol. 91, 5597-5601 (1994).
Koh et al., "Novel bis tetrahydrofuranylurethane-containing nonpeptidic protease inhibitor (PI) UIC-94017 (TMC114) with potent activity against multi-PI-resistant human immunodeficiency virus in vitro," Antimicrobial Agents and Chemotherapy, vol. 47, No. 10, 3123-3129 (2003).
Konvalinka et al., "An Active-Site Mutation in the Human Immunodeficiency Virus Type 1 Proteinase (PR) Causes Reduced PR Activity and Loss of PR-Mediated Cytotoxicity without Apparent Effect on Virus Maturation and Infectivity," Journal of Virology, vol. 69, No. 11, 7180-7186 (1995).
Kovalevsky et al., "Effectiveness of nonpeptide clinical inhibitor TMC-114 on HIV-1 protease with highly drug resistant mutations D30N, I50V, and L90M," J. Med. Chem., vol. 49, 1379-1387 (2006).
Kovalevsky et al., "Ultra-High Resolution Crystal Structure of HIV-1 Protease Mutant Reveals Two Binding Sites for Clinical Inhibitor TMC114," J. Mol. Biol., vol. 363, No. 1, 161-173 (2006).
Lapatto et al., "X-Ray Analysis of HIV-1 Proteinase and 2.7 Å Resolution Confirms Structural Homology Among Retroviral Enzymes," Nature, vol. 342, 299-302 (1989).
Levy et al., "The Folding and Dimerization of HIV-1 Protease: Evidence for a Stable Monomer from Simulations," J. Mol. Biol., vol. 340, No. 1, 67-79 (2004).
Little et al., "Antiretroviral-drug resistance among patients recently infected with HIV," New England Journal of Medicine, vol. 347, No. 6, 385-394 (2002).
Louis et al., "Revisiting Monomeric HIV-1 Protease," J. Biol. Chem., vol. 278, No. 8, 6085-6092 (2003).
Maibaum et al., "Inhibition of Porcine Pepsin by Two Substrate Analogues Containing Statine. The Effect of Histidine at the P2 Subsite on the Inhibition of Aspartic Proteinases," J. Med. Chem., vol. 31, 625-629 (1988).
Miller et al., "Ultra-potent P1 modified arylsulfonamide HIV protease inhibitors: the discovery of GW0385," Bioorganic & Medicinal Chemistry Letters, vol. 16, 1788-1794 (2006).
Miyawaki et al., "Fluorescent Indicators for $Ca^{2+}$ Based on Green Fluorescent Proteins and Calmodulin," Nature, vol. 388, No. 6645, 882-887 (1997).
Patick et al., "Antiviral and Resistance Studies of AG1343, an Orally Bioavailable Inhibitor of Human Immunodeficiency Virus Protease," Antimicrobial Agents and Chemotherapy, vol. 40, No. 2, 292-297 (1996).
Poveda et al., "Successful rescue therapy with darunabir (TMC114) in HIV-infected patients who have failed several ritonavir-boosted protease inhibitors," AIDS, vol. 20, No. 11, 1558-1560 (2006).
Prabu-Jeyabalan et al., "Mechanism of Substrate Recognition by Drug-Resistant Human Immunodeficiency Virus Type 1 Protease Variants Revealed by a Novel Structural Intermediate," Journal of Virology. vol. 80, No. 7, 3607-3616 (2006).
Sekar et al., "Fluorescence Resonance Energy Transfer (FRET) Microscopy Imaging of Live Cell Protein Localizations," J. Cell Biology, vol. 160, No. 5, 629-633 (2003).
Sepkowitz, "AIDS—the first 20 years," New England Journal of Medicine, vol. 344, No. 23, 1764-1772 (2001).
Siegel et al., "Fas Preassociation Required for Apoptosis Signaling and Dominant Inhibition by Pathogenic Mutations", Science, 2354 (2000).
Siliciano et al., "A long-term latent reservoir for HIV-1: discovery and clinical implications," Journal of Antimicrobial Chemotherapy, vol. 54, 6-9 (2004).
Simon, et al., "HIV-1 dynamics in vivo: implications for therapy," Nature Reviews Microbiology, vol. 1, 181-190 (2003).

(56) References Cited

OTHER PUBLICATIONS

Staszewski et al., "Efavirenz plus zidovudine and lamivudine, efavirenz plus indinavir, and indinavir plus zidovudine and lamivudine in the treatment of HIV-1 infection in adults," New England Journal of Medicine, 1999, 341: 1865-73.
Szczesna-Skorupa et al., "Fluorescence Resonance Energy Transfer Analysis of Cytochromes P450 2C2 and 2E1 Molecular Interactions in Living Cells," Journal of Biological Chemistry, vol. 278, 31269-31276 (2003).
Thaisrivongs et al., "Structure-Based Design of HIV Protease Inhibitors: Sulfonamide-Containing 5,6 Dihydro-4-hydroxy-2-pyrones as Non-Peptidic Inhibitors," J. Med. Chem., vol. 39, No. 22, 4349-4353 (1996).
Tie et al., "High resolution crystal structures of HIV-1 protease with a potent non-peptide inhibitor (UIC-94017) active against multi-drug-resistant clinical strains," J. Mol. Biol., vol. 338, 341-352 (2004).
Wainberg et al., "Public health implications of antiretroviral therapy and HIV drug resistance," J. Am. Med. Assoc., vol. 279, 1977-1983 (1998).
Wlodawer et al., "Conserved Folding in Retroviral Proteases: Crystal Structure of a Synthetic HIV-1 Protease," Science, vol. 245, 616-621 (1989).
Yoshimura et al., "JE-2147: a dipeptide protease inhibitor (PI) that potently inhibits multi-PI-resistant HIV-1," Proc. Natl. Acad. Sci. USA, vol. 96, 8675-8680 (1999).
Yoshimura et al., "A Potent Human Immunodeficiency Virus Type 1 Protease Inhibitor, UIC-94003 (TMC-126), and Selection of a Novel (A28S) Mutation in the Protease Active Site," Journal of Virology, vol. 76, No. 3, 1349-1358 (2002).
Youle et al., "Concomitant Use of an Active Boosted Protease Inhibitor with Enfuvirtide in Treatment-Experienced, HIV-Infected Individuals: Recent Data Consensus Recommendations," HIV Clin. Trials, vol. 7, No. 2, 86-96 (2006).
Nakamura et al., "Inhibitory Effects of Polyethers on Human Immunodeficiency Virus Replication," Antimicrob. Agents Chemother., 1992, 36(2), 492-494.
K. Ghosh et al., "Structure Based Design: Synthesis and Biological Evaluation of a Series of Novel Cycloamide-Derived HIV-1 Protease Inhibitors," J. Med. Chem., 2005, 48(10), 3576-3585.
K. Ghosh et al., "Novel Cyclourethane-Derived HIV Protease Inhibitors: A Ring Closing Olefin Metathesis Based Strategy," Bioorg. Med. Chem. Lett., 2002, 12, 1993-96.
Ghosh et al., "Stereocontrolled Synthesis of HIV-1 Protease Inhibitors with C2-Axis of Symmetry," Tetrahedron Letters 1991, 32, 5729-33.
Ghosh et al., "An Efficient Synthesis of Hydroxyethylene Dipeptide Isosteres: The Core Unit of Potent HIV-1 Protease Inhibitors," J. Org. Chem, 1991, 56, 6500-03.
Ghosh et al., "HIV-1 Protease Inhibitors: Synthesis and biological Evalution of Glycopeptides," Drug Design and Discovery 1993, 10, 77-86.
Ghosh et al., "Potent HIV-1 Protease Inhibitors : Stereoselective Synthesis of a New Dipeptide Mimic," J. Org. Chem. 1993, 58, 1025-32.
W. J. Thompson et al., "3'-Tetrahydrofuranglycine as a Novel, Unnatural Amino Acid Surrogate for Asparagine in the Design of Inhibitors of the HIV Protease," J. Am. Chem. Soc. 1993, 115, 801-03.
Ghosh et al., "3-Tetrahydrofuran and pyranyl Urethanes as High Affinity P2-Ligands for HIV-1 Protease Inhibitors," J. Med. Chem. 1993, 36, 292-94.
Ghosh et al., "Cyclic sulfones as novel and High Affinity P2-Ligands for HIV Protease Inhibitors," J. Med. Chem. 1993, 36, 924-27.
Ghosh et al., "Potent HIV Protease Inhibitors: The Development of 3'-tetrahydrofuranglycine as P2-Ligands and substituted Pyrazine Derivatives as P3-Ligands," J. Med. Chem., 1993, 36, 2300-10.
Ghosh et al., "Structure Based Design of HIV-1 Protease Inhibitors: Replacements of Two Amides and a $10\pi$ Electron Aromatic System by a Fused Bis-tetrahydrofuran" J. Med. Chem. 1994, 37, 2506-08.
Ghosh et al., "The Development of Cyclic Sulfolanes as Novel and High Affinity P2-Ligands for HIV-1 Protease Inhibitors," J. Med. Chem. 1994, 37, 1177-88.
M. K. Holloway et al., "A Priori Prediction of Activity for HIV-1 Protease Inhibitors Employing Energy Minimization in the Active Site" J. Med. Chem., 1995, 38, 305-17.
Ghosh et al., "Synthesis and Optical Resolution of High Affinity P2-Ligands for HIV-1 Protease Inhibitors," Tetrahedron Letters, 1995, 36, 505-08.
Ghosh et al., "Cyclic Sulfone-3-Carboxamide as Novel P2-ligands for HIV-1 Protease Inhibitors," Bioorganic and Med. Chem. Letters, 1995, 5, 83-88.
Ghosh et al., "Chiral Auxiliary Mediated Conjugate reduction and Asymmetric Protonation: Synthesis of High Affinity Ligands for HIV Protease Inhibitors," J. Org. Chem. 1995, 60, 6198-6201.
Ghosh et al., "A Convenient Enzymatic Route to Optically Active 1-Aminoindan-2-ol: Versatile Ligands for HIV-1 Protease Inhibitors and Asymmetric Syntheses," Synthesis 1997, 541-44.
Ghosh et al., "Asymmetric Aldol Route to Hydroxyethylamine Isostere: Stereoselective Synthesis of the Core Unit of Saquinavir," J. Org. Chem. 1997, 62, 6080-82.
Ghosh et al., "Ring-Closing Metathesis Strategy to $\alpha,\beta$-unsaturated $\gamma$- and $\delta$-Lactones: Synthesis of Hydroxyethylamine Isosteres for HIV Protease Inhibitors," Tetrahedron Letters, 1998, 8, 4651-54.
Ghosh et al., "Transition-State Mimetics for HIV Protease Inhibitors: Stereocontrolled Synthesis of Hydroxyethylene and Hydroxyethylamine Isosteres by Ester Derived Titanium Enolate Syn- and Anti-aldol Reactions," J. Org. Chem. 1998, 63, 6146-52.
Ghosh et al., "Asymmetric dihydroxylation route to a dipeptide isostere of a protease inhibitor: enantioselective synthesis of the core unit of ritonavir," Chem. Commun. 1999, 1025-26.
Ghosh et al., "2,5-Anhydro Sugar Diacid and 2,5-Anhydro Sugar Diamine Based $C_2$-Symmetric Peptidomimetics as Potential HIV-1 Protease Inhibitors," Tetrahedron Letters 2001, 42, 10121-24.
Ghosh et al., "Structure-based Design of Nonpeptide HIV Protease Inhibitors," Farmaco 2001, 56, 29-32.
Ghosh et al., "Syntheses of FDA Approved HIV Protease Inhibitors," Synthesis, 2001, 2203-29.
Ghosh et al., "Antiviral Activity of UIC-PI, a Novel Inhibitor of the Human Immunodeficiency Virus Type 1 Protease," Antiviral Research , 2002, 54, 29-36.
Ghosh et al., "Stereoselective Photochemical 1,3-Dioxolane Addition to 5-Alkoxymethyl-2(5H)-furanone: Synthesis of Bis-tetrahydrofuranyl Ligand for HIV Protease Inhibitor UIC-94017 (TMC-114)," J. Org. Chem. 2004, 69, 7822-29.
H. Gatanaga et al., "Altered HIV-1 gag Protein Interactions with Cyclophilin A (CypA) on the Acquisitionof H219Qand H219P Substitutios in the CypA Binding Loop," J. Biol. Chem. 2006, 281, 1241.
Ghosh et al., "Bis-Tetrahydrofuran: A Privileged Ligand for Darunavir and a New Generation of HIV-Protease Inhibitors That Combat Drug-Resistance. Bis-Tetrahydrofuran," ChemMedChem 2006, 1, 939-950.
Ghosh et al., "A Stereoselective Anti-aldol Route to (3R,3aS,6aR)-Tetrahydro-2H-furo[2,3-b]furan-3-ol: A Key Ligand for a New Generation of HIV Protease Inhibitors," Synthesis 2006, 3015-3019.
Tie et al., "Atomic Resolution crystal Structures of HIV-1 Protease and MutantsV82A and I84V with Saquinavir," Proteins 2007, 67, 232-242.
Wang et al., "Potent New Antiviral Compound Shows Similar inhibition and Structural Interactions with Drug Resistant Mutants and Wild Type HIV-1 Protease," J. Med. Chem. 2007, 50, 4509.
Koh et al., "Potent Inhibition of HIV-1 Replication by Novel Non-peptidyl Small Molecule Inhibitors of Protease Dimerization," J. Biol. Chem. 2007, 282, 28709.
Ghosh et al., "Darunavir, a Conceptually New HIV-1 Protease Inhibitor for the Treatment of Drug-resistant HIV," Bioorg. Med. Chem. 2007, 15, 7576.
Mitsuya et al., "Development of Protease Inhibitors and the Fight with Drug-Resistant HIV-1 Variants," Advances in Pharmacology, 2007, 56, 169-197.

(56) References Cited

OTHER PUBLICATIONS

Ghosh et al., "Design of HIV Protease Inhibitors Targeting Protein Backbone: An Effective Strategy for Combating Drug Resistance," Acc. Chem. Res. 2008, 41, 78-86.
Ghosh et al., "Enantioselective Synthesis of Cyclopentyltetrahydrofuran (Cp-THF), an Important High-Affinity P2-Ligand for HIV-1 Protease Inhibitors," Tet. Lett. 2008, 49, 3409-2412.
Ghosh et al., "Potent HIV-1 Protease Inhibitors Incorporating meso-Bicyclic Urethanes as P2-ligands: Structure-Based Design, Synthesis, Biological Evaluation and Protein-Ligand X-Ray Studies," Org. Biomol. Chem., 2008, 6, 3703-3713.
Liu et al., "Effect of Flap Mutations on Structure of HIV-1 Protease and Inhibition by Saquinavir and Darunavir," J. Mol. Biol. 2008, 381, 102-115.
Ghosh et al., "Flexible Cyclic Ethers/Polyethers as Novel P2-Ligands for HIV-1 Protease Inhibitors: Design, Synthesis, Biological Evaluation and Protein-ligand X-ray Studies," J. Med. Chem. 2008, 51, 6021-33.
Kovalevsky et al., "Solution Kinetics Measurements Suggest HIV-1 Protease Has Two Binding Sites for Darunavir and Amprenavir," J. Med. Chem. 2008, 51, 6599-03.
Kovalevsky et al., "Structural Evidence for Effectiveness of Darunavir and Two Related Antiviral Inhibitors against HIV-2 Protease," J.Mol. Biol. 2008, 384, 178-192.
Ghosh et al., "Design and Synthesis of Stereochemically Defined Novel Spirocyclic P-2-Ligands for HIV-1 Protease Inhibitors," Org. Lett. 2008, 10, 5135-38.
Koh et al., "GRL-02031: A Novel Nonpeptide Protease Inhibitor (PI) Containing a Stereochemistry Defined Fused Cyclopentanyltetrahydrofuran (Cp-THF) Potent Against Multi-PI-Resistant HIV-1 in Vitro," Antimicrobial Agents Chemother. 2009, 53, 987-996.
Ghosh et al., "Harnessing Nature's Insight: Design of Aspartyl Protease Inhibitors from Treatment of Drug-Resistant HIV to Alzheimer's Disease," J. Med. Chem. 2009, 52(8), 2163-2176.
Ghosh et al., "Design of HIV-1 Protease Inhibitors with Pyrrolidinones and Oxazolidinones as Novel P1'-Ligands to Enhance Backbone-binding interactions with Protease: Synthesis, Biological Evaluation and Protein-ligand X-ray Studies," J. Med. Chem. 2009, 52, 3902-3914.
Ghosh et al., "Structure-Based Design, Synthesis, and Biological Evaluation of a Series of Novel and Reversible Inhibitors for the Severe Acute Respiratory Syndrome-Coronavirus Papain-Like Protease," J. Med. Chem. 2009, 52 (16), 5228-5240.
Ghosh et al., Design, Synthesis, Protein-Ligand X-ray Structure, and Biological Evaluation of a Series of Novel Macrocyclic Human Immunodeficiency Virus-1 Protease Inhibitors to Combat Drug Resistance J. Med. Chem. 2009, 52 (23), 7689-7705.
Das et al.,"Prediction of Potency of Protease Inhibitors Using Free Energy Simulations with Polarizable Quantum Mechanics-Based Ligand Charges and a Hybrid Water Model," J. Chem. Info. Model, 2009, 49, 2851-2862.
Ghosh et al.,"Synthesis and biological evaluation of novel allophenylnorstatine-based HIV-1 protease inhibitors incorporating high affinity P2-ligands," Bioorg. Med. Chem. Lett. 2010, 20, 1241-1246.
Clementz et al., "Deubiquitinating and Interferon Antagonism Activities of Coronavirus Papain-Like Proteases," J. Virol. 2010, 84, 4619-4629.
Tojo et al.,"Novel Protease Inhibitors (PIs) Containing Macrocyclic Components and 3(R),3a(S),6a(R)-bis-Tetrahydrofuranylurethane (bis-THF) That Are Potent Against Multi-PI-Resistant HIV-1 Variants In Vitro," Antimicrobial Agents and Chemotherapy, 2010, 54, 3460-3470.
Ghosh et al., "Severe Acute Respiratory Syndrome Coronavirus Papain-like Novel Protease Inhibitors: Design, Synthesis, Protein-Ligand X-ray Structure and Biological Evaluation," J. Med. Chem. 2010, 53, 4968-4979.
Ghosh et al., "Darunavir (Prezista): A HIV-1 Protease Inhibitor for Treatment of Multidrug-Resistant HIV," Modern Drug Synthesis, Wiley, Edited by J. J. Li and D. S. Johnson, 2010, 29-44.
Ghosh et al., "Probing Multidrug-Resistance and Protein-Ligand Interactions with Oxatricyclic Designed Ligands in HIV-1 Protease Inhibitors,"ChemMedChem, n/a. doi: 10.1002/cmdc.201000318.
International Search Report for Application No. PCT/US09/31183, dated Mar. 11, 2009, 3 pages.
Ghosh et al., "Potent HIV Protease Inhibitors: The Development of Tetrahydrofuranylglycines as Novel P2-Ligands and Pyrazine Amides as P3-Ligands," Journal of Medicinal Chemistry, vol. 36, 1993, pp. 2300-2310.
Tie et al., "High Resolution Crystal Structures of HIV-1 Protease with a Potent-Non-Peptide Inhibitor (UIC-94017) Active Against Multi-Drug-Resistant Clinical Strains," Journal of Molecular Biology, vol. 338, 2004, pp. 341-352.
"U.S. Appl. No. 12/812,908, Final Office Action mailed Jul. 16, 2013", 7 pgs.
"U.S. Appl. No. 12/812,908, First Preliminary Amendment filed Jul. 14, 2010", 10 pgs.
"U.S. Appl. No. 12/812,908, Non Final Office Action mailed Feb. 1, 2013", 8 pgs.
"U.S. Appl. No. 12/812,908, Response filed Jun. 5, 2013 to Non Final Office Action mailed Feb. 1, 2013", 11 pgs.
"U.S. Appl. No. 12/812,908, Response filed Dec. 31, 2012 to Restriction Requirement mailed Aug. 30, 2012", 10 pgs.
"U.S. Appl. No. 12/812,908, Restriction Requirement mailed Aug. 30, 2012", 9 pgs.
"U.S. Appl. No. 12/812,908, Second Preliminary Amendment filed Jul. 14, 2010", 3 pgs.
"European Application Serial No. 09702571.2, Office Action mailed Feb. 9, 2010", 2 pgs.
"International Application Serial No. PCT/US2009/031183, International Preliminary Report on Patentability mailed Jul. 20, 2010", 8 pgs.
"International Application Serial No. PCT/US2009/031183, International Search Report mailed Mar. 11, 2009", 3 pgs.
"International Application Serial No. PCT/US2009/031183, Written Opinion mailed Mar. 11, 2009", 7 pgs.

SMALL MOLECULE INHIBITORS OF HIV PROTEASES

CROSS REFERENCE TO RELATED APPLICATIONS

This application is a divisional of U.S. patent application Ser. No. 12/812,908, filed Jul. 14, 2010, which is the U.S. national application, filed under 35 U.S.C. §371(c), of international application No. PCT/US2009/031183, filed Jan. 16, 2009, which claims priority to U.S. Provisional Patent Application No. 61/021,702 filed Jan. 17, 2008, and U.S. Provisional Application Ser. No. 61/083,744, filed Jul. 25, 2008, the disclosures of which are incorporated herein by reference.

GOVERNMENT RIGHTS

This invention was made with government support under GM053386 awarded by the National Institutes of Health. The government has certain rights in the invention.

BACKGROUND

The AIDS epidemic is one of the more challenging problems in medicine in the 21st century (United Nations. 2004 Report on the global HIV/AIDS Epidemic: 4th global report. New York, U.S.A., 2004). The disclosure of the foregoing is incorporated herein in its entirety by reference. In addition, the entirety of the disclosures of each of the publications cited herein are also incorporated herein by reference. A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is the extensive post-translational processing of precursor polyproteins by a vitally encoded protease to generate mature vital proteins required for virus assembly and function. Inhibition of this processing prevents the production of normally infectious virus. For example, Kohl, N. E. et al., Proc Nat'l Acad Sci 85:4686 (1988) demonstrated that genetic inactivation of the HIV encoded protease resulted in the production of immature, non-infectious virus particles. These results indicate that inhibition of the HIV protease represents a viable method for the treatment of AIDS and the prevention or treatment of infection by HIV.

SUMMARY OF THE INVENTION

The invention described herein includes methods for treating HIV, AIDS, and AIDS-related diseases using the compounds described herein as well as known compounds that heretofore have not been used or described as being useful in the treatment of such diseases. In addition, the invention described herein includes compounds and compositions for treating patients in need of relief from HIV, AIDS, and AIDS-related diseases.

The compounds described herein may be used in the treatment of HIV, AIDS, and AIDS-related diseases. Without being bound by theory, it is suggested that the compounds described herein may exert their utility by the inhibition of proteases encoded by human immunodeficiency virus (HIV), such as HIV-1. The compounds or pharmaceutically acceptable salts thereof, are of value in the prevention of infection by HIV, the treatment of infection by HIV and the treatment of the resulting acquired immune deficiency syndrome (AIDS), either as compounds, the pharmaceutically acceptable salts, or pharmaceutical composition ingredients. It is appreciated that the compounds described herein may be used alone or in combination with other compounds useful for treating such diseases, including those compounds that may operate by the same or different modes of action. Further, it is appreciated that the compounds and compositions described herein may be administered alone or with other compounds and compositions, such as other antiviral agents, immunomodulators, antibiotics, vaccines, and the like.

In one illustrative embodiment, the methods described herein include compounds and pharmaceutical compositions comprising compounds of the following formula (I)

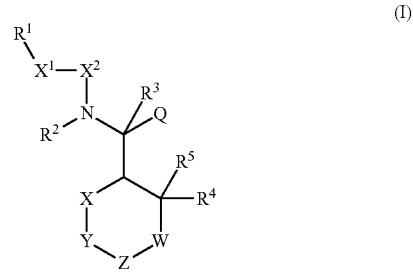

or pharmaceutically acceptable salts thereof; wherein, $X^1$ is a bond, O, or an optionally substituted nitrogen; $X^2$ is CO or $SO_2$;

$R^1$ is alkyl, cycloalkyl, heterocycle, alkenyl, heteroalkyl, cycloheteroalkyl, aryl, arylalkyl, alkylaryl, heteroaryl, heteroarylalkyl, or alkylheteroaryl, each of which is optionally substituted;

$R^2$ is selected from the group consisting of hydrogen, alkyl, heteroalkyl, hydroxy, alkoxy, arylalkoxy, amino, aminoalkyl, alkylthio, heterocyclyl, heterocyclylalkyl, aryl, heteroaryl, arylalkyl, heteroarylalkyl, and a pro-drug moiety, each of which is optionally substituted;

$R^3$ is hydrogen or alkyl;

W, X, Y, and Z are each independently selected from the group consisting of a bond, O, S, S(O), $SO_2$, optionally substituted nitrogen, optionally substituted phosphorus, $P(O)R^4$, $P(O)OR^4$, and $(CR^4R^5)_m$, where m is 1 to about 3, or Y and W and the attached atoms form an optionally substituted bicyclo-[3.2.1] ring system; providing that, when Z is O then W and Y are not O or S and when Y is O then X and Z are not O or S;

$R^4$ and $R^5$ are, in each instance, independently selected from the group consisting of hydrogen, alkyl, heteroalkyl, cycloheteroalkyl, alkenyl, alkoxy, optionally substituted amino, thioalkyl, heterocyclyl, heterocyclylalkyl, aryl, heteroaryl, arylalkyl, heteroarylalkyl, hydroxyalkyl, alkoxyalkyl, aminoalkyl, nitrile, cyanoalkyl, carboxylic acid, or a derivative thereof, and alkylcarboxylic acid, or a derivative thereof, each of which is optionally substituted; and Q is selected from the group consisting of $-CH_2OR^9$, $-CO_2R^9$, $-CONR^9R^{10}$, $-C(O)SR^9$, $-C(S)OR^9$, and $-C(S)NR^9R^{10}$; where $R^9$ and $R^{10}$ are each independently selected from the group consisting of hydrogen, alkyl, substituted alkyl, heteroalkyl, and arylalkyl; or one or both of $R^9$ and $R^{10}$ is a pro-drug moiety; or $R^9$ and $R^{10}$ together with the nitrogen to which they are attached form an optionally substituted heterocycle.

In another illustrative embodiment, the methods described herein include compounds, and pharmaceutical compositions containing such compounds of the following formula (II):

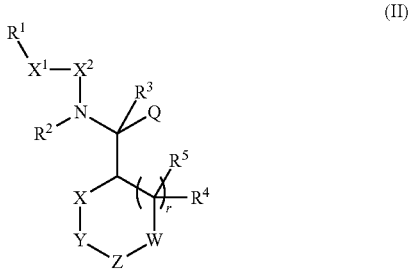

(II)

and pharmaceutically acceptable salts thereof; wherein, r is an integer from 0 to 2;

$X^1$ is a bond, O, or $NR^{14}$; and $X^2$ is CO or $SO_2$;

$R^1$ is alkyl, cycloalkyl, heterocyclyl, alkenyl, aryl, arylalkyl, alkylaryl, heteroaryl, heteroarylalkyl, or alkylheteroaryl, each of which is optionally substituted;

$R^2$ and $R^{14}$ are in each instance independently selected from the group consisting of hydrogen, alkyl, heteroalkyl, hydroxy, alkoxy, optionally substituted arylalkoxy, optionally substituted amino, optionally substituted aminoalkyl, alkylthio, heterocyclyl, heterocyclylalkyl, optionally substituted aryl, optionally substituted heteroaryl, optionally substituted arylalkyl, and optionally substituted heteroarylalkyl; either or both of $R^2$ and $R^{14}$ is a pro-drug moiety;

$R^3$ is hydrogen or alkyl;

W, X, Y, and Z are each independently selected from the group consisting of a bond, O, S, S(O), $SO_2$, $NR^4$, $PR^4$, $P(O)R^4$, $P(O)OR^4$, and $(CR^4R^5)_m$, where m is 1 to about 3; providing that, when Z is O then W and Y are not O or S and when Y is O then X and Z are not O or S;

$R^4$ and $R^5$ are, in each instance, independently selected from the group consisting of hydrogen, alkyl, heteroalkyl, alkenyl, alkoxyl, optionally substituted amino, thioalkyl, heterocyclyl, heterocyclylalkyl, optionally substituted aryl, optionally substituted heteroaryl, optionally substituted arylalkyl, optionally substituted heteroarylalkyl, $(CH_2)_pOR^8$, $(CH_2)_pN(R^8)_2$, $(CH_2)_pCN$, and $(CH_2)_pCO_2R^8$, where $R^8$ in each occurrence is independently selected from the group consisting of hydrogen, alkyl, optionally substituted arylalkyl, and a pro-drug moiety, p is an integer from 0 to 5; and Q is selected from the group consisting of $-CH_2OR^9$, $-CO_2R^9$, $-CONR^9R^{10}$, $-C(O)SR^9$, $-C(S)OR^9$, and $-C(S)NR^9R^{10}$; where $R^9$ and $R^{10}$ are each independently selected from the group consisting of hydrogen, alkyl, substituted alkyl, heteroalkyl, and arylalkyl; or one or both of $R^9$ and $R^{10}$ is a pro-drug moiety; or $R^9$ and $R^{10}$ together with the nitrogen to which they are attached form an optionally substituted heterocycle.

In another illustrative embodiment, Q is $CO_2R^9$ in each of formula (I) and/or (II). In another illustrative embodiment, $R^1$ is optionally substituted aryl in each of formula (I) and/or (II). In another illustrative embodiment, $X^1$ is O in each of formula (I) and/or (II). In another illustrative embodiment, X' is a bond in each of formula (I) and/or (II). In another illustrative embodiment, $X^2$ is $S(O)_2$ in each of formula (I) and/or (II). In another illustrative embodiment, $X^2$ is C(O) in each of formula (I) and/or (II). In another illustrative embodiment, $R^2$ is H in each of formula (I) and/or (II). In another illustrative embodiment, $R^3$ is H in each of formula (I) and/or (II). In another illustrative embodiment, W, X, Y, and Z are taken together with the attached carbons to form a 5 to 8 membered heterocycle containing 1 or 2 oxygen atoms, or 1 oxygen and 1 nitrogen atom, such as but not limited to tetrahydrofuran, dioxolane, tetrahydropyran, dioxane, morpholine, oxepane, each of which is optionally substituted, in each of formula (I) and/or (II). In another illustrative embodiment, $R^4$ and $R^5$ are each independently selected from H, alkyl, CN, aryl, heteroaryl, heteroalkyl, such as ethers, amines, and the like, arylalkyl, arylheteroalkyl, heterocyclyl, each of which is optionally substituted, in each of formula (I) and/or (II). In another illustrative embodiment, one or more of $R^4$ and $R^5$ is alkyl substituted with a carboxylic acid or derivative thereof in each of formula (I) and/or (II). It is to be understood that each of the foregoing illustrative embodiments may be combined with others in other embodiments of the invention described herein. Illustratively, in another embodiment, Q is $CO_2R^9$, $R^1$ is optionally substituted aryl, $X^1$ is a bond, and $X^2$ is $S(O)_2$ in each of formula (I) and/or (II). Other combinations of the foregoing embodiments are also described herein.

In another illustrative embodiment, the methods described herein include compounds and pharmaceutical compositions comprising compounds of the following formula (III)

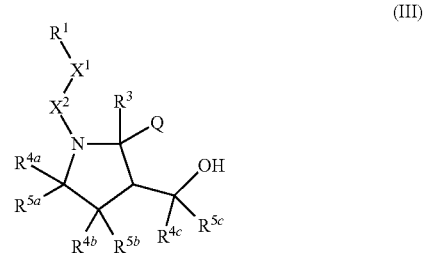

(III)

or pharmaceutically acceptable salts thereof; wherein, $X^1$ is a bond, O, or an optionally substituted nitrogen; $X^2$ is CO or $SO_2$;

$R^1$ is alkyl, cycloalkyl, alkenyl, heteroalkyl, heterocyclyl, heterocyclylalkyl, aryl, arylalkyl, heteroaryl, or heteroarylalkyl, each of which is optionally substituted;

$R^3$ is hydrogen or alkyl;

each of $R^{4a}$, $R^{4b}$, and $R^{4c}$, and each of $R^{5a}R^{5ba}$, and $R^{5c}$ are independently selected in each instance from the group consisting of hydrogen, alkyl, heteroalkyl, alkenyl, alkoxy, amino, aminoalkyl, thioalkyl, heterocyclyl, heterocyclylalkyl, aryl, heteroaryl, arylalkyl, heteroarylalkyl, hydroxyalkyl, nitrile, cyanoalkyl, carboxylic acid or a derivative thereof, and alkylcarboxylic acid or a derivative thereof, each of which is optionally substituted; or any two of $R^{4a}$, $R^{4b}$, $R^{4c}$, $R^{5a}R^{5ba}$, and $R^{5c}R^4$ and $R^5$ are taken together with the attached atoms to form a carbocycle or heterocycle; and Q is a carboxylic acid or a derivative thereof.

In another illustrative embodiment, Q is $CO_2R^9$ in each of formula (I), (II), and/or (III). In another illustrative embodiment, $R^1$ is optionally substituted aryl in each of formula (I), (II), and/or (III). In another illustrative embodiment, $X^1$ is O in each of formula (I), (II), and/or (III). In another illustrative embodiment, X' is a bond in each of formula (I), (II), and/or (III). In another illustrative embodiment, $X^2$ is $S(O)_2$ in each of formula (I), (II), and/or (III). In another illustrative embodiment, $X^2$ is C(O) in each of formula (I), (II), and/or (III). In another illustrative embodiment, $R^3$ is H in each of formula (I), (II), and/or (III). It is to be understood that each of the foregoing illustrative embodiments may be combined with others in other embodiments of the invention described herein. Illustratively, in another embodiment, Q is $CO_2R^9$, $R^1$ is optionally substituted aryl, $X^1$ is a bond, and $X^2$ is $S(O)_2$ in each of formula (I), (II), and/or (III). Other combinations of the foregoing embodiments are also described herein.

Without being bound by theory, it is suggested that in one aspect, the compounds described herein, may be inhibiting proteases required for effective viral replication by mimicking a transition state, such as the tetrahedral transition state of amide hydrolysis. Without being bound by theory, it is suggested that in another aspect, the compounds described herein, may be inhibiting or interfering with viral replication by inhibiting dimerization of the protease.

DETAILED DESCRIPTION

In one illustrative embodiment, the methods described herein include compounds and pharmaceutical compositions comprising compounds of the following formula

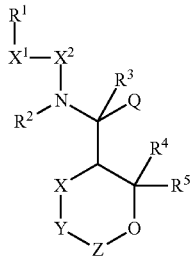

and pharmaceutically acceptable salts thereof; wherein, $X^1$ is a bond, O, or an optionally substituted nitrogen; $X^2$ is $CO$ or $SO_2$;

$R^1$ is alkyl, cycloalkyl, alkenyl, heteroalkyl, heterocyclyl, heterocyclylalkyl, aryl, arylalkyl, heteroaryl, or heteroarylalkyl, each of which is optionally substituted;

$R^2$ is selected from the group consisting of hydrogen, alkyl, heteroalkyl, hydroxy, alkoxy, arylalkoxy, amino, alkylthio, heterocyclyl, heterocyclylalkyl, aryl, heteroaryl, arylalkyl, heteroarylalkyl, and pro-drug moieties, each of which is optionally substituted;

$R^3$ is hydrogen or alkyl;

X, Y, and Z are taken together with the attached atoms to form a heterocycle or heterobicycle, each of which is optionally substituted;

$R^4$ and $R^5$ are, in each instance, independently selected from the group consisting of hydrogen, alkyl, heteroalkyl, alkenyl, alkoxy, amino, aminoalkyl, thioalkyl, heterocyclyl, heterocyclylalkyl, aryl, heteroaryl, arylalkyl, heteroarylalkyl, hydroxyalkyl, nitrile, cyanoalkyl, carboxylic acid or a derivative thereof, and alkylcarboxylic acid or a derivative thereof, each of which is optionally substituted; or $R^4$ and $R^5$ are taken together with the attached atoms to form a carbocycle or heterocycle; and Q is selected from the group consisting of heteroalkyl, hydroxyalkyl, and carboxylic acid or a derivative thereof.

In another illustrative embodiment, the methods described herein include compounds and pharmaceutical compositions comprising compounds of the following formula

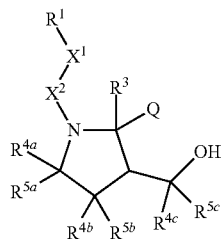

and pharmaceutically acceptable salts thereof; wherein, $X^1$ is a bond, O, or an optionally substituted nitrogen; $X^2$ is $CO$ or $SO_2$;

$R^1$ is alkyl, cycloalkyl, alkenyl, heteroalkyl, heterocyclyl, heterocyclylalkyl, aryl, arylalkyl, heteroaryl, or heteroarylalkyl, each of which is optionally substituted;

$R^3$ is hydrogen or alkyl;

each of $R^{4a}$, $R^{4b}$, and $R^{4c}$, and each of $R^{5a}R^{5ba}$, and $R^{5c}$ are independently selected in each instance from the group consisting of hydrogen, alkyl, heteroalkyl, alkenyl, alkoxy, amino, aminoalkyl, thioalkyl, heterocyclyl, heterocyclylalkyl, aryl, heteroaryl, arylalkyl, heteroarylalkyl, hydroxyalkyl, nitrile, cyanoalkyl, carboxylic acid or a derivative thereof, and alkylcarboxylic acid or a derivative thereof, each of which is optionally substituted; or any two of $R^{4a}$, $R^{4b}$, $R^{4c}$, $R^{5a}R^{5ba}$, and $R^{5c}R^4$ and $R^5$ are taken together with the attached atoms to form a carbocycle or heterocycle; and Q is a carboxylic acid or a derivative thereof.

In another illustrative embodiment, the methods described herein include compounds and pharmaceutical compositions wherein Z is selected from the group consisting of a bond, S(O), $SO_2$, optionally substituted nitrogen, and $(CR^4R^5)_m$, where m is 1 to about 3. In another illustrative embodiment, the methods described herein include compounds and pharmaceutical compositions wherein X and Y are each independently selected from the group consisting of a bond, O, S, S(O), $SO_2$, optionally substituted nitrogen, and $(CR^4R^5)_m$, where m is 1 to about 3; providing that, when X is O then Y is not O or S and when Y is O then X is not O or S. In another illustrative embodiment, the methods described herein include compounds and pharmaceutical compositions wherein W, X, Y, and Z are taken together with the attached carbons to form a 5 to 8 membered heterocycle containing 1 or 2 oxygen atoms. In another illustrative embodiment, the methods described herein include compounds and pharmaceutical compositions wherein W, X, Y, and Z are taken together with the attached carbons to form a 5 to 8 membered heterocycle containing 1 oxygen and 1 nitrogen atom. In another illustrative embodiment, the methods described herein include compounds and pharmaceutical compositions wherein the heterocycle is a tetrahydrofuran, dioxolane, tetrahydropyran, dioxane, morpholine, oxepane, each of which is optionally substituted.

In another illustrative embodiment, the methods described herein include compounds and pharmaceutical compositions wherein the heterobicycle is a oxabicyclo-[3.2.1]-octane, which is optionally substituted. In another embodiment, the optionally substituted oxabicyclo-[3.2.1]-octane is substituted with an optionally substituted fused phenyl.

In another illustrative embodiment, the methods described herein include compounds and pharmaceutical compositions wherein one of X, Y, or Z is O or $NR^{2a}$, where $R^{2a}$ is selected from the group consisting of hydrogen, alkyl, heteroalkyl, hydroxy, alkoxy, arylalkoxy, amino, alkylthio, heterocyclyl, heterocyclylalkyl, aryl, heteroaryl, arylalkyl, heteroarylalkyl, and pro-drug moieties, each of which is optionally substituted; and the others of X, Y, and Z are selected from the group consisting of a bond and $(CR^4R^5)_m$, where m is 1 to about 3.

In another illustrative embodiment, the methods described herein include compounds and pharmaceutical compositions wherein X is O; and Y and Z are each $(CR^4R^5)_m$, where m is 1 to about 3; and Z is a bond. In another illustrative embodiment, the methods described herein include compounds and pharmaceutical compositions wherein Y is O; and X and Z are each $(CR^4R^5)_m$, where m is 1 to about 3. In another illustrative embodiment, the methods described herein include compounds and pharmaceutical compositions wherein one of X is O; Y is a bond, and Z is $(CR^4R^5)_m$, where m is 1 to about 3. In another illustrative embodiment, the methods described herein include compounds and pharmaceutical compositions wherein each of X, Y, and Z is $(CR^4R^5)_m$, where m is 1. In another illustrative embodiment, the methods described herein include compounds and pharmaceutical compositions wherein each of X and Y is $(CR^4R^5)_m$, where m is 1; and Z is a bond.

In another illustrative embodiment, the methods described herein include compounds and pharmaceutical compositions wherein Q is selected from the group consisting of —CH$_2$OR$^9$, —CO$_2$R$^9$, —CONR$^9$R$^{10}$, —C(O)SR$^9$, —C(S)OR$^9$, and —C(S)NR$^9$R$^{10}$; where R$^9$ and R$^{10}$ are each independently selected from the group consisting of hydrogen, alkyl, substituted alkyl, heteroalkyl, and arylalkyl; or one or both of R$^9$ and R$^{10}$ is a pro-drug moiety; or R$^9$ and R$^{10}$ together with the nitrogen to which they are attached form an optionally substituted heterocycle. In another illustrative embodiment, the methods described herein include compounds and pharmaceutical compositions wherein Q is CO$_2$R$^9$.

In another illustrative embodiment, the methods described herein include compounds and pharmaceutical compositions wherein R$^1$ is optionally substituted aryl.

In another illustrative embodiment, the methods described herein include compounds and pharmaceutical compositions wherein X$^1$ is O and X$^2$ is C(O). In another illustrative embodiment, the methods described herein include compounds and pharmaceutical compositions wherein X is a bond. In another illustrative embodiment, the methods described herein include compounds and pharmaceutical compositions wherein X$^2$ is S(O)$_2$. In another illustrative embodiment, the methods described herein include compounds and pharmaceutical compositions wherein X$^1$ is a bond and X$^2$ is S(O)$_2$. In another illustrative embodiment, the methods described herein include compounds and pharmaceutical compositions wherein X$^1$ is O. In another illustrative embodiment, the methods described herein include compounds and pharmaceutical compositions wherein X$^2$ is C(O).

In another illustrative embodiment, the methods described herein include compounds and pharmaceutical compositions wherein R$^2$ is H. In another illustrative embodiment, the methods described herein include compounds and pharmaceutical compositions wherein R$^3$ is H. In another illustrative embodiment, the methods described herein include compounds and pharmaceutical compositions wherein R$^4$ and R$^5$ are each independently selected from H, alkyl, CN, aryl, heteroaryl, heteroalkyl, such as ethers, amines, and the like, arylalkyl, arylheteroalkyl, heterocyclyl, each of which is optionally substituted. In another illustrative embodiment, the methods described herein include compounds and pharmaceutical compositions wherein one or more of R$^4$ and R$^5$ is alkyl substituted with a carboxylic acid or derivative thereof.

In another illustrative embodiment, the methods described herein include compounds and pharmaceutical compositions wherein Q is CO$_2$R$^9$, R$^1$ is optionally substituted aryl, X$^1$ is a bond, and X$^2$ is S(O)$_2$.

In another illustrative embodiment, the methods described herein include compounds and pharmaceutical compositions of the formula

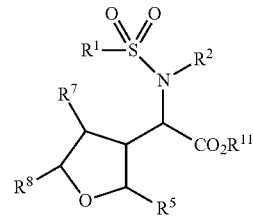

and pharmaceutically acceptable salts thereof; wherein

R$^5$ is selected from the group consisting of hydrogen, alkyl, heteroalkyl, cycloheteroalkyl, alkenyl, alkoxy, optionally substituted amino, thioalkyl, heterocyclyl, heterocyclylalkyl, aryl, heteroaryl, arylalkyl, heteroarylalkyl, hydroxyalkyl, alkoxyalkyl, aminoalkyl, nitrile, cyanoalkyl, carboxylic acid, or a derivative thereof, and alkylcarboxylic acid, or a derivative thereof, each of which is optionally substituted;

R$^7$ is selected from the group consisting of hydrogen, hydroxy, alkoxy optionally substituted alkyl, heteroalkyl, optionally substituted alkylaryl, optionally substituted arylalkyl, optionally substituted alkylheteroaryl, optionally substituted heteroarylalkyl, and NR$^9$R$^{10}$, where R$^9$ and R$^{10}$ are each independently selected from the group consisting of hydrogen, alkyl, substituted alkyl, heteroalkyl, and arylalkyl; or R$^9$ and R$^{10}$ together with the nitrogen to which they are attached form an optionally substituted heterocyclyl; and R$^8$ is selected from the group consisting of hydrogen, alkyl, cycloalkyl, heterocyclyl, alkenyl, aryl, arylalkyl, alkylaryl, heteroaryl, heteroarylalkyl, and alkylheteroaryl, each of which is optionally substituted;

R$^{11}$ is hydrogen, alkyl, arylalkyl or pro-drug moiety.

In another illustrative embodiment, the methods described herein include compounds and pharmaceutical compositions comprising compounds of the following formula

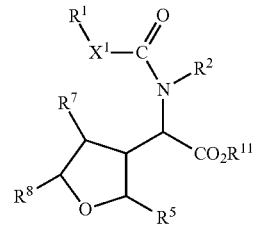

and pharmaceutically acceptable salts thereof; wherein

X$^1$ is a bond, optionally substituted nitrogen or O;

R$^2$ is selected from the group consisting of hydrogen, alkyl, heteroalkyl, hydroxy, alkoxy, arylalkoxy, amino, aminoalkyl, alkylthio, heterocyclyl, heterocyclylalkyl, aryl, heteroaryl, arylalkyl, heteroarylalkyl, and a pro-drug moiety, each of which is optionally substituted;

R$^5$ is selected from the group consisting of hydrogen, alkyl, heteroalkyl, cycloheteroalkyl, alkenyl, alkoxy, optionally substituted amino, thioalkyl, heterocyclyl, heterocyclylalkyl, aryl, heteroaryl, arylalkyl, heteroarylalkyl, hydroxyalkyl, alkoxyalkyl, aminoalkyl, nitrile, cyanoalkyl, carboxylic acid, or a derivative thereof, and alkylcarboxylic acid, or a derivative thereof, each of which is optionally substituted;

$R^7$ is hydrogen, alkyl, alkenyl, heteroalkyl, alkylaryl, arylalkyl, alkylheteroaryl, heteroarylalkyl, alkoxy or $NR^9R^{10}$, each of which is optionally substituted, where $R^9$ and $R^{10}$ are each independently selected from the group consisting of hydrogen, alkyl, substituted alkyl, heteroalkyl, and arylalkyl; or $R^9$ and $R^{10}$ together with the nitrogen to which they are attached form an optionally substituted heterocycle; and $R^8$ is selected from the group consisting of hydrogen, alkyl, cycloalkyl, heterocyclyl, alkenyl, aryl, arylalkyl, alkylaryl, heteroaryl, heteroarylalkyl, and alkylheteroaryl, each of which is optionally substituted; and $R^{11}$ is selected from the group consisting of hydrogen, alkyl, arylalkyl, and pro-drug moiety.

In another illustrative embodiment, the methods described herein include compounds and pharmaceutical compositions wherein $R^8$ is aryl. In another illustrative embodiment, the methods described herein include compounds and pharmaceutical compositions wherein $R^8$ is naphthyl, quinolinyl or phenyl, each of which is optionally substituted.

In another illustrative embodiment, the methods described herein include compounds and pharmaceutical compositions of the formula

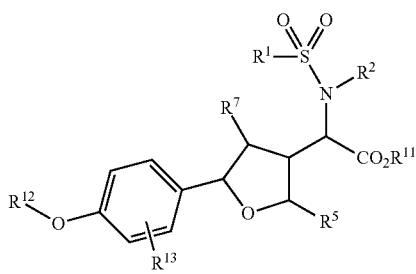

and pharmaceutically acceptable salts thereof; wherein $R^1$ is optionally substituted aryl; $R^2$ is selected from the group consisting of hydrogen, alkyl, heteroalkyl, hydroxy, alkoxy, arylalkoxy, amino, aminoalkyl, alkylthio, heterocyclyl, heterocyclylalkyl, aryl, heteroaryl, arylalkyl, heteroarylalkyl, and a pro-drug moiety, each of which is optionally substituted;

$R^5$ is selected from the group consisting of hydrogen, alkyl, heteroalkyl, cycloheteroalkyl, alkenyl, alkoxy, optionally substituted amino, thioalkyl, heterocyclyl, heterocyclyl alkyl, aryl, heteroaryl, arylalkyl, heteroarylalkyl, hydroxyalkyl, alkoxyalkyl, aminoalkyl, nitrile, cyanoalkyl, carboxylic acid, or a derivative thereof, and alkylcarboxylic acid, or a derivative thereof, each of which is optionally substituted;

$R^7$ is hydrogen, alkyl, alkenyl, heteroalkyl, alkylaryl, arylalkyl, alkylheteroaryl, heteroarylalkyl, alkoxy or $NR^9R^{10}$, each of which is optionally substituted, where $R^9$ and $R^{10}$ are each independently selected from the group consisting of hydrogen, alkyl, substituted alkyl, heteroalkyl, and arylalkyl; or $R^9$ and $R^{10}$ together with the nitrogen to which they are attached form an optionally substituted heterocycle;

$R^{12}$ and $R^{11}$ are each independently selected from the group consisting of hydrogen, alkyl, arylalkyl and pro-drug moiety; and $R^{13}$ is from one to three substituents, each independently selected from the group consisting of hydrogen, alkyl, haloalkyl, heteroalkyl, halogen, arylalkyl, optionally substituted amino, alkoxyl, alkylsulfonyl, arylsulfonyl, alkylsulfinyl, arylsulfinyl, alkylthio, nitro, $C(O)OR^9$ and $C(O)NR^9R^{10}$.

In another illustrative embodiment, the methods described herein include compounds and pharmaceutical compositions comprising compounds of the following formula

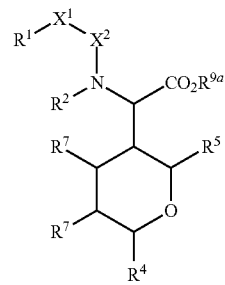

and pharmaceutically acceptable salts thereof; wherein $R^7$ is independently selected in each instance from hydrogen, optionally substituted alkyl, heteroalkyl, optionally substituted alkylaryl, optionally substituted arylalkyl, optionally substituted alkylheteroaryl, optionally substituted heteroarylalkyl, $OR^9$ or $NR^9R^{10}$, where $R^9$ and $R^{10}$ are each independently selected from the group consisting of hydrogen, alkyl, substituted alkyl, heteroalkyl, and arylalkyl; or $R^9$ and $R^{10}$ together with the nitrogen to which they are attached form an optionally substituted heterocycle; and $R^{9a}$ is hydrogen, alkyl, arylalkyl or pro-drug.

In another illustrative embodiment, the methods described herein include compounds and pharmaceutical compositions comprising compounds of the above wherein R' aryl or heteroaryl, each of which is optionally substituted.

In another illustrative embodiment, the methods described herein include compounds and pharmaceutical compositions comprising compounds of the above formula wherein $X^1$ is a bond, O, or $NR^{14}$; $X^2$ is CO or $SO_2$; $R^1$ is alkyl, cycloalkyl, heterocyclyl, alkenyl, aryl, arylalkyl, alkylaryl, heteroaryl, heteroarylalkyl, or alkylheteroaryl, each of which is optionally substituted; $R^2$ is selected from the group consisting of hydrogen, alkyl, heteroalkyl, hydroxy, alkoxy, optionally substituted arylalkoxy, optionally substituted amino, optionally substituted aminoalkyl, alkylthio, heterocyclyl, heterocyclylalkyl, optionally substituted aryl, optionally substituted heteroaryl, optionally substituted arylalkyl, optionally substituted heteroarylalkyl, and a pro-drug moiety; and $R^4$ is aryl or heteroaryl, each of which is optionally substituted;

In another illustrative embodiment, the methods described herein include compounds and pharmaceutical compositions comprising compounds of the above formula wherein $X^1$ is a bond, O, or $NR^{14}$; $X^2$ is CO or $SO_2$; and $R^1$ is alkyl, cycloalkyl, heterocyclyl, alkenyl, aryl, arylalkyl, alkylaryl, heteroaryl, heteroarylalkyl, or alkylheteroaryl, each of which is optionally substituted; $R^2$ is hydrogen; $R^{14}$ is selected from the group consisting of hydrogen, alkyl, heteroalkyl, hydroxy, alkoxy, optionally substituted arylalkoxy, optionally substituted amino, optionally substituted aminoalkyl, alkylthio, heterocyclyl, heterocyclylalkyl, optionally substituted aryl, optionally substituted heteroaryl, optionally substituted arylalkyl, optionally substituted heteroarylalkyl, and a pro-drug moiety.

In another illustrative embodiment, the compounds of following formula are described

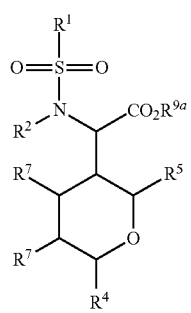

and pharmaceutically acceptable salts thereof; wherein $R^1$ is optionally substituted aryl; $R^2$ is hydrogen, alkyl, heteroalkyl, hydroxy, alkoxy, optionally substituted arylalkoxy, optionally substituted amino, optionally substituted aminoalkyl, alkylthio, heterocyclyl, heterocyclylalkyl, optionally substituted aryl, optionally substituted heteroaryl, optionally substituted arylalkyl, optionally substituted heteroarylalkyl, or a pro-drug moiety;

$R^4$ is selected from the group consisting of hydrogen, alkyl, cycloalkyl, heterocyclyl, alkenyl, aryl, arylalkyl, alkylaryl, heteroaryl, heteroarylalkyl, and alkylheteroaryl; $R^5$ is selected from the group consisting of hydrogen, nitrile, alkyl, cycloalkyl, heterocyclyl, alkenyl, aryl, arylalkyl, alkylaryl, heteroaryl, heteroarylalkyl, alkylheteroaryl, $(CH_2)p\text{-}OR^8$, $(CH_2)p\text{-}CO_2R^8$, and $(CH_2)p\text{-}NHR^8$, where p is an integer from 0 to 5, and $R^8$ in each instance is independently selected from the group consisting of hydrogen, alkyl, optionally substituted arylalkyl, and pro-drug moiety; $R^7$ is hydrogen, optionally substituted alkyl, heteroalkyl, optionally substituted alkylaryl, optionally substituted arylalkyl, optionally substituted alkylheteroaryl, optionally substituted heteroarylalkyl, $OR^9$ or $NR^9R^{10}$, where $R^9$ and $R^{10}$ are each independently selected from the group consisting of hydrogen, alkyl, substituted alkyl, heteroalkyl, and arylalkyl; or $R^9$ and $R^{10}$ together with the nitrogen to which they are attached form an optionally substituted heterocycle; and $R^{11}$ is hydrogen, alkyl, arylalkyl or pro-drug moiety.

In another illustrative embodiment, the compounds of the following formula are described:

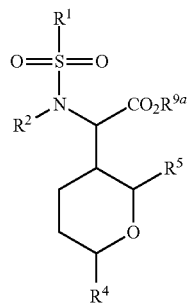

and pharmaceutically acceptable salts thereof; wherein $R^1$ is alkyl, cycloalkyl, heterocyclyl, alkenyl, aryl, arylalkyl, alkylaryl, heteroaryl, heteroarylalkyl, or alkylheteroaryl, each of which is optionally substituted;

$R^2$ and $R^4$ are each independently selected in each instance from the group consisting of hydrogen, alkyl, cycloalkyl, heterocyclyl, alkenyl, aryl, arylalkyl, alkylaryl, heteroaryl, heteroarylalkyl, and alkylheteroaryl; $R^5$ is selected from the group consisting of hydrogen, nitrile, alkyl, cycloalkyl, heterocyclyl, alkenyl, aryl, arylalkyl, alkylaryl, heteroaryl, heteroarylalkyl; Q is an alcohol or a derivative thereof.

In another illustrative embodiment, the compounds of following formula are described

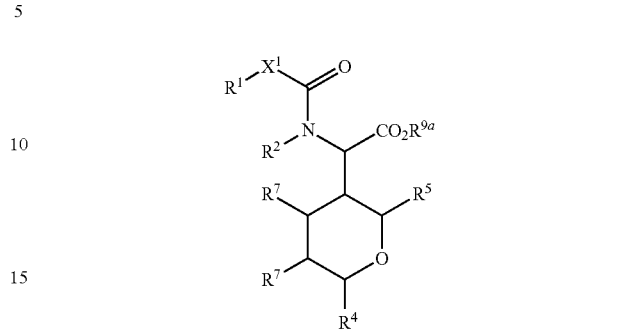

and pharmaceutically acceptable salts thereof; wherein $R^1$ is optionally substituted aryl;

$X^1$ is a bond, $NR^{14}$ or O; $R^2$ and $R^{14}$ are in each instance independently selected from the group consisting of hydrogen, alkyl, heteroalkyl, hydroxy, alkoxy, optionally substituted arylalkoxy, optionally substituted amino, optionally substituted aminoalkyl, alkylthio, heterocyclyl, heterocyclylalkyl, optionally substituted aryl, optionally substituted heteroaryl, optionally substituted arylalkyl, optionally substituted heteroarylalkyl, and a pro-drug moiety;

$R^4$ is selected from the group consisting of hydrogen, alkyl, cycloalkyl, heterocyclyl, alkenyl, aryl, arylalkyl, alkylaryl, heteroaryl, heteroarylalkyl, and alkylheteroaryl;

$R^5$ is selected from the group consisting of hydrogen, nitrile, alkyl, cycloalkyl, heterocyclyl, alkenyl, aryl, arylalkyl, alkylaryl, heteroaryl, heteroarylalkyl, alkylheteroaryl, $(CH_2)p\text{-}OR^8$, $(CH_2)p\text{-}CO_2R^8$, and $(CH_2)p\text{-}NHR^8$, where p is an integer from 0 to 5, and $R^8$ in each instance is independently selected from the group consisting of hydrogen, alkyl, optionally substituted arylalkyl, and pro-drug moiety, with the proviso that at least one of $R^4$ or $R^5$ is not hydrogen;

$R^7$ is independently selected in each instance from hydrogen, optionally substituted alkyl, heteroalkyl, optionally substituted alkylaryl, optionally substituted arylalkyl, optionally substituted alkylheteroaryl, optionally substituted heteroarylalkyl, $OR^9$ or $NR^9R^{10}$, where $R^9$ and $R^{10}$ are each independently selected from the group consisting of hydrogen, alkyl, substituted alkyl, heteroalkyl, and arylalkyl; or $R^9$ and $R^{10}$ together with the nitrogen to which they are attached form an optionally substituted heterocycle; and $R^{11}$ is hydrogen, alkyl, arylalkyl or pro-drug moiety.

In another illustrative embodiment, the methods described herein include compounds and pharmaceutical compositions wherein $R^5$ is allyl or hydrogen.

In another illustrative embodiment, the methods described herein include compounds and pharmaceutical compositions of the formula

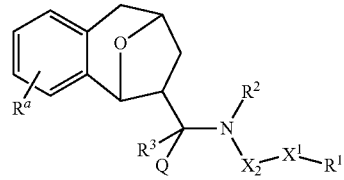

and pharmaceutically acceptable salts thereof; wherein $R^a$ represents from 0 to 3 substituents independently selected in each instance from hydroxy, alkyl, heteroalkyl, alkoxy, aryl, arylalkyl, hydroxy, optionally substituted amino, and thioalkyl, each of which is optionally substituted, or two vicinal $R^a$ together with the attached carbons form a fused ring.

In another illustrative embodiment, the methods described herein include compounds and pharmaceutical compositions wherein $X^2$ is $SO_2$; $X^1$ is a bond; $R^3$ is hydrogen; $R^1$ is aryl; and Q is a carboxylic acid or a derivative thereof.

In another illustrative embodiment, the methods described herein include compounds and pharmaceutical compositions of the formula

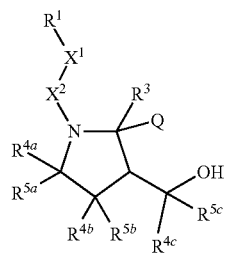

and pharmaceutically acceptable salts thereof; wherein $X^1$ is a bond, O, or an optionally substituted nitrogen; $X^2$ is CO or $SO_2$;

$R^1$ is alkyl, cycloalkyl, alkenyl, heteroalkyl, heterocyclyl, heterocyclylalkyl, aryl, arylalkyl, heteroaryl, or heteroarylalkyl, each of which is optionally substituted;

$R^3$ is hydrogen or alkyl;

each of $R^{4a}$, $R^{4b}$, and $R^{4c}$, and each of $R^{5a}R^{5ba}$, and $R^{5c}$ are independently selected in each instance from the group consisting of hydrogen, alkyl, heteroalkyl, alkenyl, alkoxy, amino, aminoalkyl, thioalkyl, heterocyclyl, heterocyclylalkyl, aryl, heteroaryl, arylalkyl, heteroarylalkyl, hydroxyalkyl, nitrile, cyanoalkyl, carboxylic acid or a derivative thereof, and alkylcarboxylic acid or a derivative thereof, each of which is optionally substituted; or any two of $R^{4a}$, $R^{4b}$, $R^{4c}$, $R^{5a}R^{5ba}$ and $R^{5c}R^4$ and $R^5$ are taken together with the attached atoms to form a carbocycle or heterocycle; and Q is a carboxylic acid or a derivative thereof.

In another illustrative embodiment, the methods described herein include compounds and pharmaceutical compositions wherein Q is selected from the group consisting of —$CH_2OR^9$, —$CO_2R^9$, —$CONR^9R^{10}$, —$C(O)SR^9$, —$C(S)OR^9$, and —$C(S)NR^9R^{10}$; where $R^9$ and $R^{10}$ are each independently selected from the group consisting of hydrogen, alkyl, substituted alkyl, heteroalkyl, and arylalkyl; or one or both of $R^9$ and $R^{10}$ is a pro-drug moiety; or $R^9$ and $R^{10}$ together with the nitrogen to which they are attached form an optionally substituted heterocycle. In another illustrative embodiment, the methods described herein include compounds and pharmaceutical compositions wherein Q is $CO_2R^9$.

In another illustrative embodiment, the methods described herein include compounds and pharmaceutical compositions wherein $R^1$ is optionally substituted aryl. In another illustrative embodiment, the methods described herein include compounds and pharmaceutical compositions wherein $R^1$ is substituted phenyl. In another illustrative embodiment, the methods described herein include compounds and pharmaceutical compositions wherein $R^1$ is optionally substituted aryl.

In another illustrative embodiment, the methods described herein include compounds and pharmaceutical compositions wherein $X^1$ is O and $X^2$ is C(O). In another illustrative embodiment, the methods described herein include compounds and pharmaceutical compositions wherein $X^1$ is a bond. In another illustrative embodiment, the methods described herein include compounds and pharmaceutical compositions wherein $X^2$ is $S(O)_2$. In another illustrative embodiment, the methods described herein include compounds and pharmaceutical compositions wherein $X^1$ is a bond and $X^2$ is $S(O)_2$. In another illustrative embodiment, the methods described herein include compounds and pharmaceutical compositions wherein $X^1$ is O. In another illustrative embodiment, the methods described herein include compounds and pharmaceutical compositions wherein $X^2$ is C(O).

In another illustrative embodiment, the methods described herein include compounds and pharmaceutical compositions wherein $R^3$ is H.

In another illustrative embodiment, the methods described herein include compounds and pharmaceutical compositions comprising compounds of the following formula

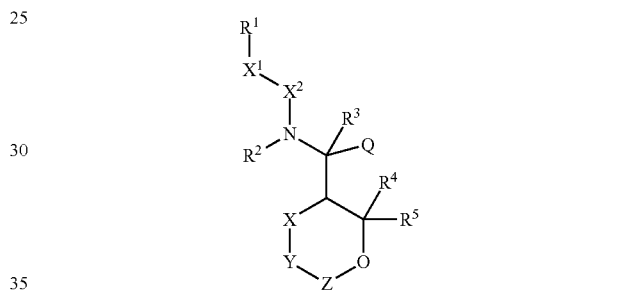

and pharmaceutically acceptable salts thereof; wherein $X^1$ is a bond, O, or an optionally substituted nitrogen; $X^2$ is CO or $SO_2$;

$R^1$ is alkyl, cycloalkyl, alkenyl, heteroalkyl, heterocyclyl, heterocyclylalkyl, aryl, arylalkyl, heteroaryl, or heteroarylalkyl, each of which is optionally substituted;

$R^2$ is selected from the group consisting of hydrogen, alkyl, heteroalkyl, hydroxy, alkoxy, arylalkoxy, amino, alkylthio, heterocyclyl, heterocyclylalkyl, aryl, heteroaryl, arylalkyl, heteroarylalkyl, and pro-drug moieties, each of which is optionally substituted;

$R^3$ is hydrogen or alkyl;

X, Y, and Z are taken together with the attached atoms to form a heterocycle or heterobicycle, each of which is optionally substituted;

$R^4$ and $R^5$ are, in each instance, independently selected from the group consisting of hydrogen, alkyl, heteroalkyl, alkenyl, alkoxy, amino, aminoalkyl, thioalkyl, heterocyclyl, heterocyclylalkyl, aryl, heteroaryl, arylalkyl, heteroarylalkyl, hydroxyalkyl, nitrile, cyanoalkyl, carboxylic acid or a derivative thereof, and alkylcarboxylic acid or a derivative thereof, each of which is optionally substituted; or $R^4$ and $R^5$ are taken together with the attached atoms to form a carbocycle or heterocycle; and Q is selected from the group consisting of heteroalkyl, hydroxyalkyl, and carboxylic acid or a derivative thereof;

providing that the compound is not a compound of the formulae

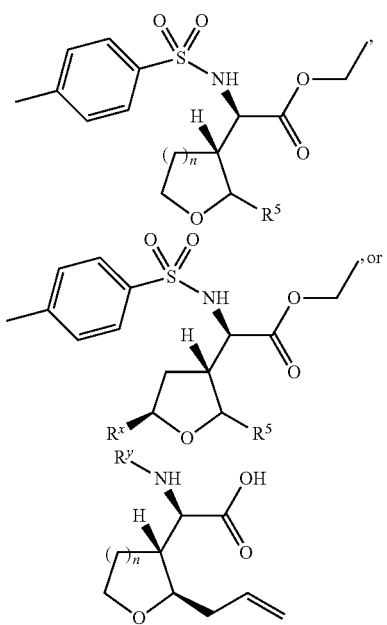

wherein $R^5$ is hydrogen, cyano or $CH_2CH=CH_2$; n is 1 or 2; $R^x$ is 1-naphthyl or phenyl; and $R^y$ is tosyl or hydrogen.

In another illustrative embodiment, the methods described herein include compounds and pharmaceutical compositions comprising compounds of the following formula

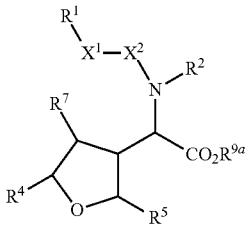

and pharmaceutically acceptable salts thereof; wherein $X^1$ is a bond, O, or $NR^{14}$; $X^2$ is CO or $SO_2$;

$R^1$ is alkyl, cycloalkyl, heterocyclyl, alkenyl, aryl, arylalkyl, alkylaryl, heteroaryl, heteroarylalkyl, or alkylheteroaryl, each of which is optionally substituted;

$R^2$ and $R^{14}$ are in each instance independently selected from the group consisting of hydrogen, alkyl, heteroalkyl, hydroxy, alkoxy, optionally substituted arylalkoxy, optionally substituted amino, optionally substituted aminoalkyl, alkylthio, heterocyclyl, heterocyclylalkyl, optionally substituted aryl, optionally substituted heteroaryl, optionally substituted arylalkyl, optionally substituted heteroarylalkyl, and a pro-drug moiety;

$R^4$ is selected from the group consisting of hydrogen, alkyl, cycloalkyl, heterocyclyl, alkenyl, aryl, arylalkyl, alkylaryl, heteroaryl, heteroarylalkyl, and alkylheteroaryl;

$R^5$ is selected from the group consisting of hydrogen, nitrile, alkyl, cycloalkyl, heterocyclyl, alkenyl, aryl, arylalkyl, alkylaryl, heteroaryl, heteroarylalkyl, alkylheteroaryl, $(CH_2)p-OR^8$, $(CH_2)p-CO_2R^8$, and $(CH_2)p-NHR^8$, where p is an integer from 0 to 5, and $R^8$ in each instance is independently selected from the group consisting of hydrogen, alkyl, optionally substituted arylalkyl, and pro-drug moiety;

$R^7$ is hydrogen, optionally substituted alkyl, heteroalkyl, optionally substituted alkylaryl, optionally substituted arylalkyl, optionally substituted alkylheteroaryl, optionally substituted heteroarylalkyl, $OR^9$ or $NR^9R^{10}$, where $R^9$ and $R^{10}$ are each independently selected from the group consisting of hydrogen, alkyl, substituted alkyl, heteroalkyl, and arylalkyl; or $R^9$ and $R^{10}$ together with the nitrogen to which they are attached form an optionally substituted heterocycle; and $R^{9a}$ is hydrogen, alkyl, arylalkyl or pro-drug In another illustrative embodiment, the methods described herein include compounds and pharmaceutical compositions comprising compounds of the above wherein $R^1$ aryl or heteroaryl, each of which is optionally substituted.

In another illustrative embodiment, the methods described herein include compounds and pharmaceutical compositions comprising compounds of the above formula wherein $X^1$ is a bond, O, or $NR^{14}$; $X^2$ is CO or $SO_2$; $R^1$ is alkyl, cycloalkyl, heterocyclyl, alkenyl, aryl, arylalkyl, alkylaryl, heteroaryl, heteroarylalkyl, or alkylheteroaryl, each of which is optionally substituted; $R^2$ is selected from the group consisting of hydrogen, alkyl, heteroalkyl, hydroxy, alkoxy, optionally substituted arylalkoxy, optionally substituted amino, optionally substituted aminoalkyl, alkylthio, heterocyclyl, heterocyclylalkyl, optionally substituted aryl, optionally substituted heteroaryl, optionally substituted arylalkyl, optionally substituted heteroarylalkyl, and a pro-drug moiety; and $R^4$ is aryl or heteroaryl, each of which is optionally substituted;

In another illustrative embodiment, the methods described herein include compounds and pharmaceutical compositions comprising compounds of the above formula wherein $X^1$ is a bond, O, or $NR^{14}$; $X^2$ is CO or $SO_2$; and $R^1$ is alkyl, cycloalkyl, heterocyclyl, alkenyl, aryl, arylalkyl, alkylaryl, heteroaryl, heteroarylalkyl, or alkylheteroaryl, each of which is optionally substituted; $R^2$ is hydrogen; $R^{14}$ is selected from the group consisting of hydrogen, alkyl, heteroalkyl, hydroxy, alkoxy, optionally substituted arylalkoxy, optionally substituted amino, optionally substituted aminoalkyl, alkylthio, heterocyclyl, heterocyclylalkyl, optionally substituted aryl, optionally substituted heteroaryl, optionally substituted arylalkyl, optionally substituted heteroarylalkyl, and a pro-drug moiety.

In another illustrative embodiment, the compounds of following formula are described;

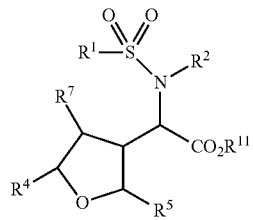

wherein $R^1$ is optionally substituted aryl; $R^2$ is hydrogen, alkyl, heteroalkyl, hydroxy, alkoxy, optionally substituted arylalkoxy, optionally substituted amino, optionally substituted aminoalkyl, alkylthio, heterocyclyl, heterocyclylalkyl, optionally substituted aryl, optionally substituted heteroaryl, optionally substituted arylalkyl, optionally substituted heteroarylalkyl, or a pro-drug moiety;

$R^4$ is selected from the group consisting of hydrogen, alkyl, cycloalkyl, heterocyclyl, alkenyl, aryl, arylalkyl, alkylaryl, heteroaryl, heteroarylalkyl, and alkylheteroaryl; $R^5$ is selected from the group consisting of hydrogen, nitrite, alkyl, cycloalkyl, heterocyclyl, alkenyl, aryl, aryl alkyl, alkylaryl, heteroaryl, heteroarylalkyl, alkylheteroaryl, (CH$_2$)p-OR$^8$, (CH$_2$)p-CO$_2$R$^8$, and (CH$_2$)p-NHR$^8$, where p is an integer from 0 to 5, and R$^8$ in each instance is independently selected from the group consisting of hydrogen, alkyl, optionally substituted arylalkyl, and pro-drug moiety; R$^7$ is hydrogen, optionally substituted alkyl, heteroalkyl, optionally substituted alkylaryl, optionally substituted arylalkyl, optionally substituted alkylheteroaryl, optionally substituted heteroarylalkyl, OR$^9$ or NR$^9$R$^{10}$, where R$^9$ and R$^{10}$ are each independently selected from the group consisting of hydrogen, alkyl, substituted alkyl, heteroalkyl, and arylalkyl; or R$^9$ and R$^{10}$ together with the nitrogen to which they are attached form an optionally substituted heterocycle; and R$^{11}$ is hydrogen, alkyl, arylalkyl or pro-drug moiety.

In another illustrative embodiment, the compounds of the following formula are described:

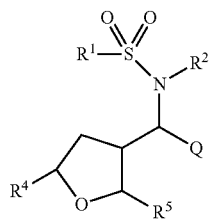

wherein R$^1$ is alkyl, cycloalkyl, heterocyclyl, alkenyl, aryl, arylalkyl, alkylaryl, heteroaryl, heteroarylalkyl, or alkylheteroaryl, each of which is optionally substituted;

R$^2$ and R$^4$ are each independently selected in each instance from the group consisting of hydrogen, alkyl, cycloalkyl, heterocyclyl, alkenyl, aryl, arylalkyl, alkylaryl, heteroaryl, heteroarylalkyl, and alkylheteroaryl; R$^5$ is selected from the group consisting of hydrogen, nitrile, alkyl, cycloalkyl, heterocyclyl, alkenyl, aryl, arylalkyl, alkylaryl, heteroaryl, heteroarylalkyl; Q is an alcohol or a derivative thereof.

In another illustrative embodiment, the compounds of following formula are described;

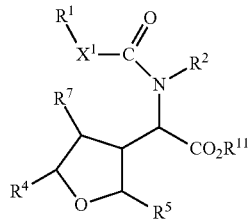

wherein R$^1$ is optionally substituted aryl;

X$^1$ is a bond, NR$^{14}$ or O; R$^2$ and R$^{14}$ are in each instance independently selected from the group consisting of hydrogen, alkyl, heteroalkyl, hydroxy, alkoxy, optionally substituted arylalkoxy, optionally substituted amino, optionally substituted aminoalkyl, alkylthio, heterocyclyl, heterocyclylalkyl, optionally substituted aryl, optionally substituted heteroaryl, optionally substituted arylalkyl, optionally substituted heteroarylalkyl, and a pro-drug moiety;

R$^1$ is optionally substituted aryl;

X$^1$ is a bond, NR$^{14}$ or O; R$^2$ and R$^{14}$ are in each instance independently selected from the group consisting of hydrogen, alkyl, heteroalkyl, hydroxy, alkoxy, optionally substituted arylalkoxy, optionally substituted amino, optionally substituted aminoalkyl, alkylthio, heterocyclyl, heterocyclylalkyl, optionally substituted aryl, optionally substituted heteroaryl, optionally substituted arylalkyl, optionally substituted heteroarylalkyl, and a pro-drug moiety;

R$^7$ is hydrogen, optionally substituted alkyl, heteroalkyl, optionally substituted alkylaryl, optionally substituted arylalkyl, optionally substituted alkylheteroaryl, optionally substituted heteroarylalkyl, OR$^9$ or NR$^9$R$^{10}$, where R$^9$ and R$^{10}$ are each independently selected from the group consisting of hydrogen, alkyl, substituted alkyl, heteroalkyl, and arylalkyl; or R$^9$ and R$^{10}$ together with the nitrogen to which they are attached form an optionally substituted heterocycle; and R$^{11}$ is hydrogen, alkyl, arylalkyl or pro-drug moiety.

As used herein the term amino generally refers to primary, secondary, and tertiary amino groups, including but not limited to NH2, alkylamino, dialkylamino, arylalkylamino, and the like.

As used herein the term carboxylic acid derivative generally refers to esters, amides, including primary, secondary, and tertiary amides, acyl hydrazides, hydroxamic acids and esters, cyano, and the like.

As used herein the term heteroalkyl generally refers to straight-chain or branched alkyl groups where one or more carbon atoms are replaced by a heteroatom, such as oxygen, nitrogen, sulfur, and the like, and includes but is not limited to alkoxyalkyl, alkylaminoalkyl, alkylaminoalkyloxyalkyl, alkylthioalkyl, and the like.

As used herein the term substituted when applied to aryl, heteroaryl, and the like generally refers to halo, alkyl, alkoxy, heteroalkyl, aryl, heteroaryl, arylalkyl, heteroarylalkyl, hydroxy, amino, alkyl and aryl sulfonyl, sulfonamide, and the like]

As used herein the term substituted when applied to alkyl, heteroalkyl, cycloalkyl, and the like generally refers to halo, alkyl, alkoxy, heteroalkyl, aryl, heteroaryl, arylalkyl, heteroarylalkyl, hydroxy, amino, alkyl and aryl sulfonyl, sulfonamide, and the like]

In another embodiment, optional substituents in each of the foregoing include those found on optionally substituted aryl and heteroaryl include one or more groups selected from alkyl, alkoxy, amino, which may be mono or dialkylated, or acylated, aryl, arylalkyl, halo, heteroalkyl, heteroalkoxy, cyano, nitro, and the like. In one embodiment, heteroalkyl includes alkoxyalkyl, aminoalkyl, where the amino group may be mono or dialkylated, or acylated, haloalkyl, haloalkoxyalkyl, and the like.

The above formula includes compounds that are described in Ghosh et al. (Organic Letters 7:7-10 (2005)), the entirety of the disclosure of which is incorporated herein by reference. Ghosh et al. also described suitable methods for preparing the compounds described herein. As such, the compounds described in Ghosh et al. are not included in the novel compounds described herein. However, the compounds of Ghosh et al. are included in the methods described herein for treating HIV, AIDS, and related diseases and disease states.

In one embodiment of the compounds described herein, the following compounds are not included:

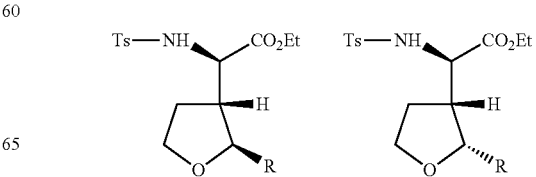

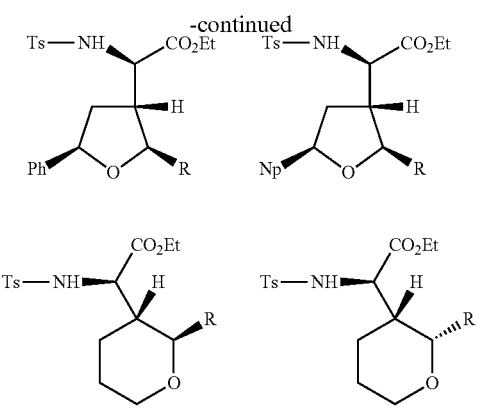

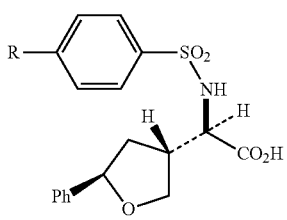

where Ts=tosyl, Ph=phenyl, Np=naphthyl, and R=H, CN, or allyl. In one illustrative embodiment of the methods described herein, one or more of the foregoing compounds is included in the pharmaceutical compositions or used in the methods described herein, including the corresponding carboxylic acids and derivatives thereof, including thiocarboxylic acids and esters, thionocarboxylic acids and esters, amides, thioamides, and the like.

In another illustrative embodiment, the compounds of the following formula are described:

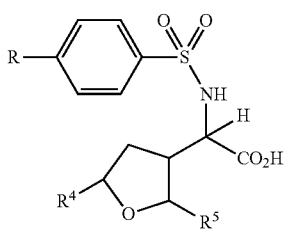

wherein R is alkyl, including methyl, amino, or alkoxy, including methoxy.

In another illustrative embodiment, the compounds of the following formula are described:

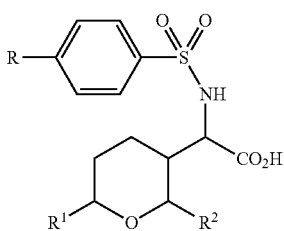

wherein R=alkyl; $R^4$=Ph, Ar, alkyl, heteroalkyl or heteroaryl group, and
$R^5$=alkyl, including Me;
R=alkoxy, including methoxy; $R^4$=Ph, Ar, alkyl, heteroalkyl and heteroaryl group, and
$R^5$=alkyl, including Me; $R^4$=Ph, Ar, alkyl, heteroalkyl and heteroaryl group;
R=NH$_2$; $R^4$=Ph, Ar, alkyl, heteroalkyl and heteroaryl group, and
$R^5$=alkyl, including Me; $R^4$=Ph, Ar, alkyl, heteroalkyl and heteroaryl group; or
R=$R^4$=Ph, Ar, alkyl, heteroalkyl and heteroaryl group, and
$R^5$=alkyl, including Me; $R^4$=Ph, Ar, alkyl, heteroalkyl and heteroaryl group.

In another illustrative embodiment, the compounds of the following formulae are described:

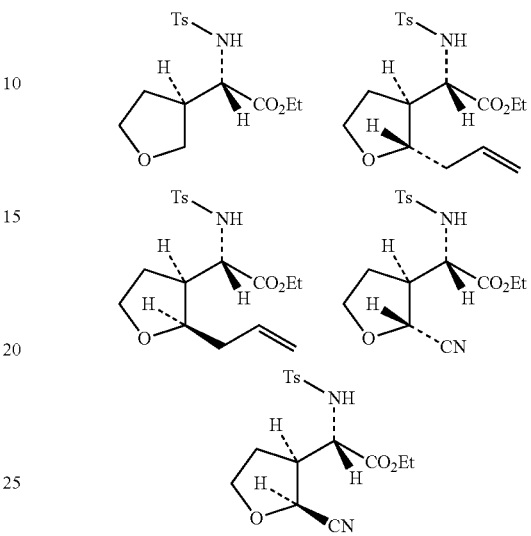

where Ts is a tosyl group (4-Me-PhSO$_2$).

In another illustrative embodiment, the compounds of the following formula are described:

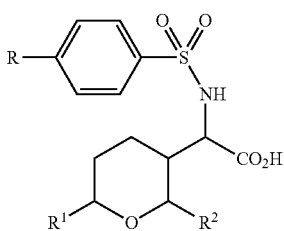

wherein R=hydrogen or alkyl; $R^1$=hydrogen, Ph, Ar, alkyl, heteroalkyl or heteroaryl group, and $R^2$=alkyl, including Me; $R^1$=Ph, Ar, alkyl, heteroalkyl and heteroaryl group; or R=alkoxy, including methoxy; and $R^2$=alkyl, including Me; $R^1$=Ph, Ar, alkyl, heteroalkyl and heteroaryl group; or R=NH$_2$; $R^1$=Ph, Ar, alkyl, heteroalkyl and heteroaryl group, and $R^2$=alkyl, including Me; or R=$R^1$=Ph, Ar, alkyl, heteroalkyl and heteroaryl group, and $R^2$=alkyl, including Me; $R^1$=Ph, Ar, alkyl, heteroalkyl and heteroaryl group.

In another illustrative embodiment, the compounds of the following formulae are described:

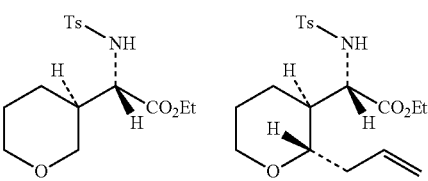

-continued

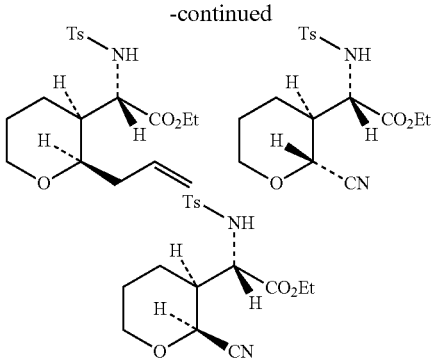

In another illustrative embodiment, the compounds of the following formula are described:

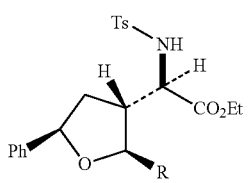

wherein, for example, R=H, CN, $(CH_2)p$-$OR^8$, $(CH_2)p$-$CO_2R^8$, $(CH_2)p$-$NHR^8$, and the like; p is an integer from 0 to 5; where $R^8$ in each occurrence is independently selected from hydrogen, alkyl, and optionally substituted arylalkyl, or one or more $R^8$ is a pro-drug moiety.

In another illustrative embodiment, the compounds of the following formula are described:

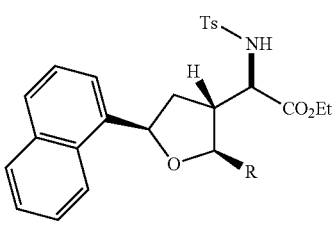

wherein, for example, R=H, CN, $(CH_2)p$-$OR^8$, $(CH_2)p$-$CO_2R^8$, $(CH_2)p$-$NHR^8$, and the like, where p is an integer from 0 to 5; and $R^8$ in each occurrence is independently selected from H, alkyl, and optionally substituted arylalkyl, or one or more $R^8$ is a pro-drug moiety.

In another illustrative embodiment, the compounds of the following formulae are described:

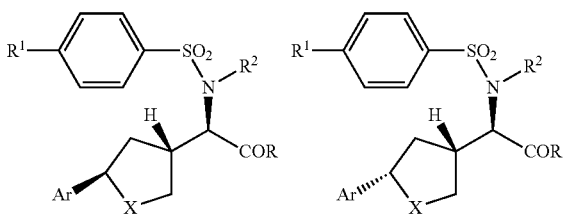

wherein X is selected from O, S, S(O), $SO_2$, $NR^4$, $PR^4$, $P(O)R^4$, $P(O)OR^4$, and $C(R^4R^5)$; and is illustratively O.

Ar=Ph, or substituted phenyl, such as, but not limited to alkoxyphenyl, including p-, m-, and o-anisolyl, 3,4-benzodioxanyl, 3,4-benzodioxolanyl, and the like;

$R^1$=H, alkyl, $NH_2$, alkoxy, $CH_2OH$;

$R^2$=H, $CH_2CHMe_2$, $(CH_2)_2CHMe_2$; and

R=OH, $OR^8$, $NHR^8$, wherein each occurrence is independently selected from H, alkyl, such as, but not limited to, methyl and ethyl, and optionally substituted arylalkyl including, but not limited to, benzyl, or one or more $R^8$ is a pro-drug moiety.

In another illustrative embodiment, the compounds of the following formulae are described;

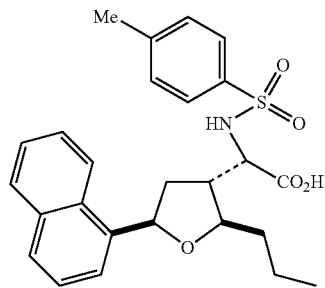

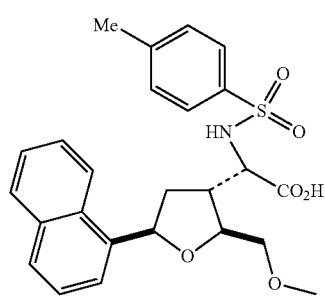

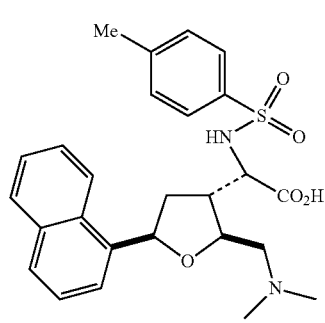

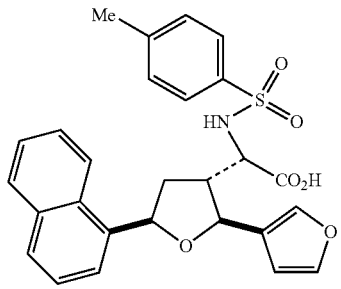

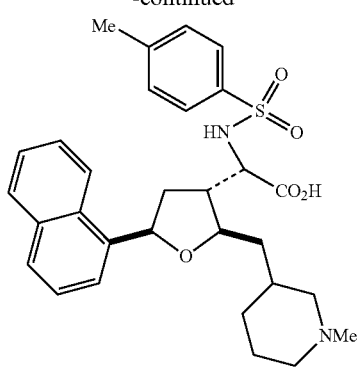
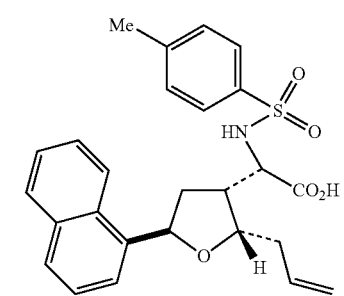
In another illustrative embodiment, the compounds of following formulae are described;
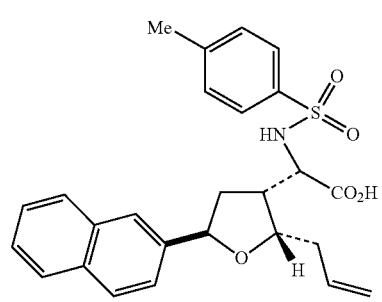
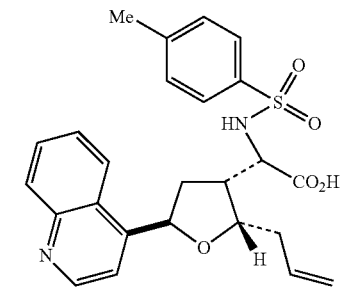 [SMILES: C=CC[C@@H]1O[C@@H](c2cccc3ccccc23)CC1[C@H](NS(=O)(=O)c1ccc(C)cc1)C(=O)O]
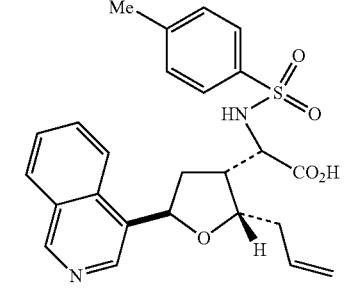
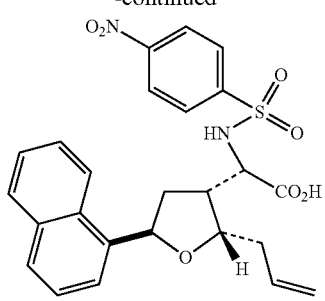
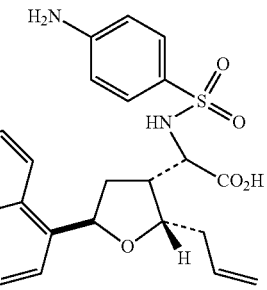
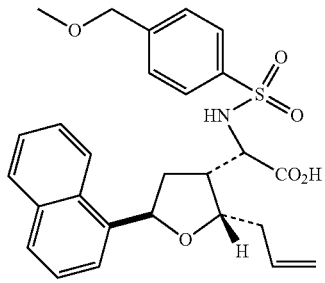
In another illustrative embodiment, the compounds of the following formulae are described;
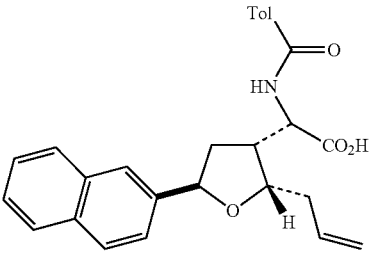
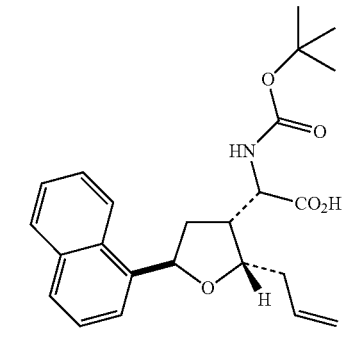

-continued

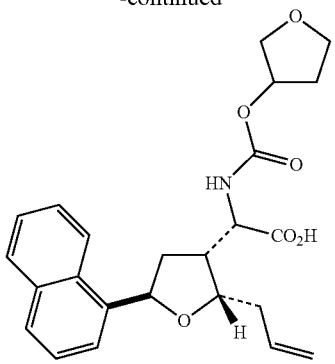

In another illustrative embodiment, the compounds of the following formula are described:

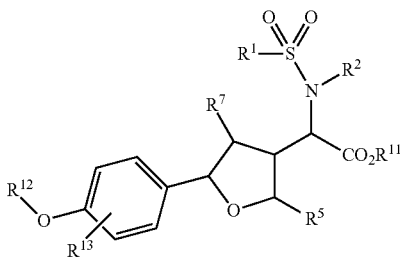

$R^1$ is optionally substituted aryl; $R^2$ is hydrogen, alkyl, heteroalkyl, hydroxy, alkoxy, optionally substituted arylalkoxy, optionally substituted amino, optionally substituted aminoalkyl, alkylthio, heterocyclyl, heterocyclylalkyl, optionally substituted aryl, optionally substituted heteroaryl, optionally substituted arylalkyl, optionally substituted heteroarylalkyl, or a pro-drug moiety; $R^5$ is selected from the group consisting of hydrogen, nitrile, alkyl, cycloalkyl, heterocyclyl, alkenyl, aryl, alkylaryl, arylalkyl, heteroaryl, heteroarylalkyl, and alkylheteroaryl; $R^7$ is hydrogen, optionally substituted alkyl, heteroalkyl, optionally substituted alkylaryl, optionally substituted arylalkyl, optionally substituted alkylheteroaryl, optionally substituted heteroarylalkyl, $OR^9$ or $NR^9R^{10}$; where $R^9$ and $R^{10}$ are each independently selected from the group consisting of hydrogen, alkyl, substituted alkyl, heteroalkyl, and arylalkyl; or $R^9$ and $R^{10}$ together with the nitrogen to which they are attached form an optionally substituted heterocycle; $R^{12}$ and $R^{11}$ are each independently selected from the group consisting of hydrogen, alkyl, arylalkyl and pro-drug moiety; and $R^{13}$ is from one to three substituents independently selected from the group consisting of hydrogen, alkyl, haloalkyl, heteroalkyl, halogen, arylalkyl, optionally substituted amino, alkoxyl, alkylsulfonyl, arylsulfonyl, alkylsulfinyl, arylsulfinyl, alkylthio, nitro, $C(O)OR^9$ and $C(O)NR^9R^{10}$.

In another illustrative embodiment, the compounds of the following formula are described:

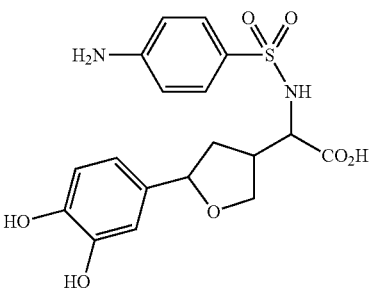 [SMILES: Nc1ccc(S(=O)(=O)NC(C(=O)O)C2COC(c3ccc(O)c(O)c3)C2)cc1]

In another illustrative embodiment, the compounds of the following formula are described:

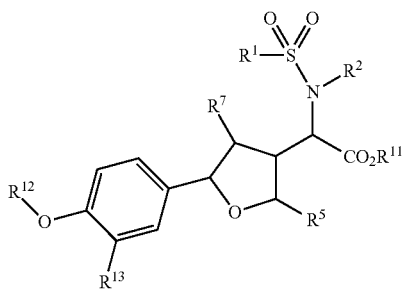

$R^1$ is optionally substituted aryl; $R^2$ is hydrogen, alkyl, heteroalkyl, hydroxy, alkoxy, optionally substituted arylalkoxy, optionally substituted amino, optionally substituted aminoalkyl, alkylthio, heterocyclyl, heterocyclyl alkyl, optionally substituted aryl, optionally substituted heteroaryl, optionally substituted arylalkyl, optionally substituted heteroarylalkyl, or a pro-drug moiety; $R^5$ is selected from the group consisting of hydrogen, nitrile, alkyl, cycloalkyl, heterocyclyl, alkenyl, aryl, alkylaryl, arylalkyl, heteroaryl, heteroarylalkyl, and alkylheteroaryl; $R^7$ is hydrogen, optionally substituted alkyl, heteroalkyl, optionally substituted alkylaryl, optionally substituted arylalkyl, optionally substituted alkylheteroaryl, optionally substituted heteroarylalkyl, $OR^9$ or $NR^9R^{10}$; where $R^9$ and $R^{10}$ are each independently selected from the group consisting of hydrogen, alkyl, substituted alkyl, heteroalkyl, and arylalkyl; or $R^9$ and $R^{10}$ together with the nitrogen to which they are attached form an optionally substituted heterocycle; $R^{12}$ and $R^{11}$ are each independently selected from the group consisting of hydrogen, alkyl, arylalkyl and pro-drug moiety; and $R^{13}$ is hydroxyl or $OR^9$.

In another illustrative embodiment, the compounds of the following formula are described:

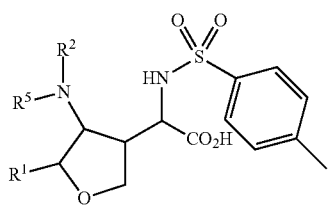

$R^1$ is optionally substituted aryl; $R^2$ is hydrogen, alkyl, heteroalkyl, hydroxy, alkoxy, optionally substituted arylalkoxy, optionally substituted amino, optionally substituted aminoalkyl, alkylthio, heterocyclyl, heterocyclylalkyl, optionally substituted aryl, optionally substituted heteroaryl, optionally substituted arylalkyl, optionally substituted heteroarylalkyl, or a pro-drug moiety; and R[5] is selected from the group consisting of hydrogen, alkyl, cycloalkyl, heterocyclyl, alkenyl, aryl, alkylaryl, arylalkyl, heteroaryl, heteroarylalkyl, and alkylheteroaryl.

In another illustrative embodiment, the compounds of the following formula are described:

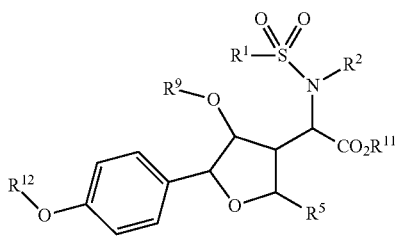

R[1] is optionally substituted aryl; R[2] is hydrogen, alkyl, heteroalkyl, hydroxy, alkoxy, optionally substituted arylalkoxy, optionally substituted amino, optionally substituted aminoalkyl, alkylthio, heterocyclyl, heterocyclylalkyl, optionally substituted aryl, optionally substituted heteroaryl, optionally substituted arylalkyl, optionally substituted heteroarylalkyl, or a pro-drug moiety; R[5] is selected from the group consisting of hydrogen, nitrile, alkyl, cycloalkyl, heterocyclyl, alkenyl, aryl, alkylaryl, arylalkyl, heteroaryl, heteroarylalkyl, and alkylheteroaryl; R[9] is selected from the group consisting of hydrogen, alkyl, substituted alkyl, heteroalkyl, and arylalkyl; R[12] and R[11] are each independently selected from the group consisting of hydrogen, alkyl, arylalkyl and pro-drug moiety.

In another illustrative embodiment, the compounds of the following formula are described

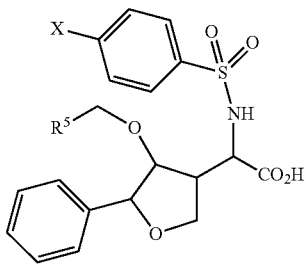

R[5] is selected from the group consisting of hydrogen, alkyl, cycloalkyl, heterocyclyl, alkenyl, aryl, alkylaryl, arylalkyl, heteroaryl, heteroarylalkyl, and alkylheteroaryl; and X is hydroxyl or amino.

In another illustrative embodiment, the compounds of the following formula are described

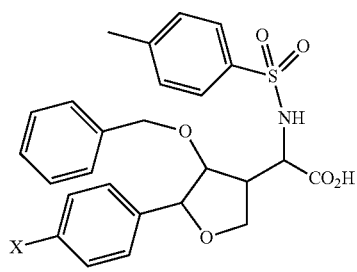

X is hydroxyl or amino.

In another illustrative embodiment, the compounds of the following formula are described:

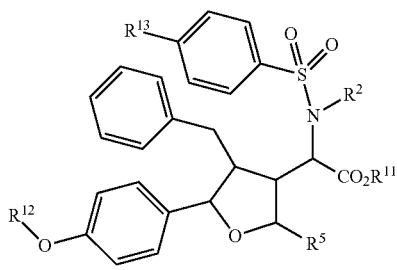

R[2] is hydrogen, alkyl, heteroalkyl, hydroxy, alkoxy, optionally substituted arylalkoxy, optionally substituted amino, optionally substituted aminoalkyl, alkylthio, heterocyclyl, heterocyclylalkyl, optionally substituted aryl, optionally substituted heteroaryl, optionally substituted arylalkyl, optionally substituted heteroarylalkyl, or a pro-drug moiety; R[5] is selected from the group consisting of hydrogen, nitrile, alkyl, cycloalkyl, heterocyclyl, alkenyl, aryl, alkylaryl, arylalkyl, heteroaryl, heteroarylalkyl, and alkylheteroaryl; R[12] and R[11] are each independently selected from the group consisting of hydrogen, alkyl, arylalkyl and pro-drug moiety; and R[13] is from one to three substituents independently selected from the group consisting of hydrogen, alkyl, heteroalkyl, halogen, arylalkyl, optionally substituted amino, alkoxyl, alkylsulfonyl, arylsulfonyl, alkylsulfinyl, arylsulfinyl, alkylthio, nitro, C(O)OR[9] and C(O)NR[9]R[10] where R[9] and R[10] are each independently selected from the group consisting of hydrogen, alkyl, substituted alkyl, heteroalkyl, and arylalkyl.

In another illustrative embodiment, the compounds of the following formula are described:

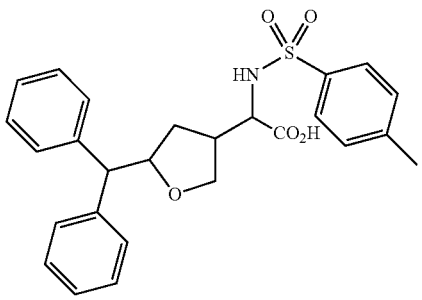 [SMILES: Cc1ccc(S(=O)(=O)NC(C(=O)O)C2COC(C(c3ccccc3)c3ccccc3)C2)cc1]

In another illustrative embodiment, the compounds of the following formula are described:

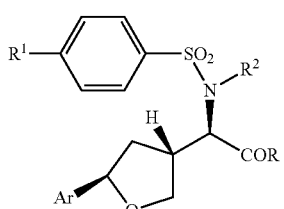

wherein Ar in an optionally substituted aryl group, Ph, alkoxyphenyl, including p, m, and o-anisole, 3,4-benzodioxan, 3,4-benzodioxolan, and the like;

$R^1$=$NH_2$, alkoxy, $CH_2OH$, and the like;

$R^2$=H, $CH_2CHMe_2$, $(CH2)_2CHMe_2$, and the like; and

R=OH, $OR^8$, $NHR^8$, wherein $R^8$ in each occurrence is independently selected from hydrogen, alkyl, including methyl and ethyl, and optionally substituted arylalkyl including benzyl, or one or more $R^8$ is a pro-drug moiety.

In another illustrative embodiment, the compounds of the following formula are described:

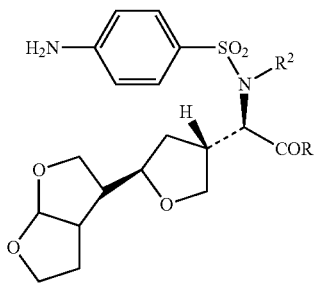

wherein R=OH, $OR^8$, $NHR^8$, wherein $R^8$ in each occurrence is independently selected from hydrogen, alkyl, including methyl and ethyl, and optionally substituted arylalkyl including benzyl, or one or more $R^8$ is a pro-drug moiety.

It is also appreciated that in the foregoing embodiments, certain aspects of the compounds are presented in the alternative, such as selections for any one or more of R, $X^1$, $X^2$, $R^1$, $R^2$, $R^3$, $R^4$, $R^5$, $R^6$, $R^7$, $R^8$, $R^9$, $R^{10}$, $R^{11}$, $R^{12}$, n, m, and p. It is therefore to be understood that various alternate embodiments of the invention include individual members of those lists, as well as the various subsets of those lists. Each of those combinations is to be understood to be described herein by way of the lists.

In one embodiment, the following illustrative method for preparing compounds described herein is as follows:

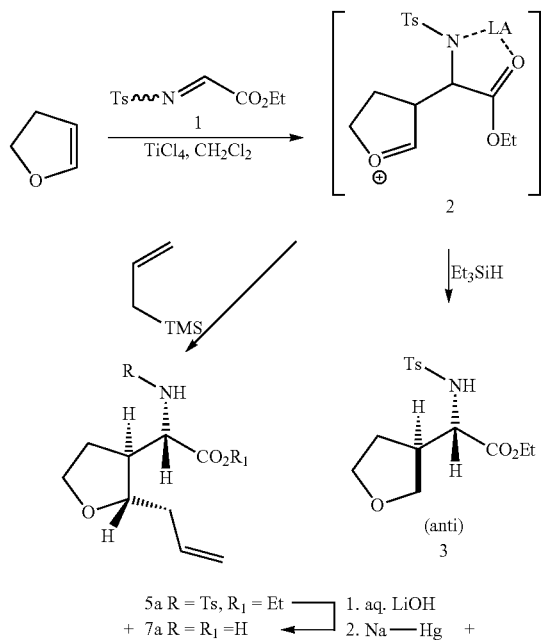

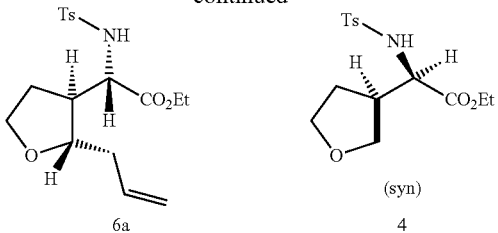

as described by Ghosh et al. It is to be understood that the above synthetic method is adaptable to prepare the entire range of compounds described herein by the appropriate selection of the corresponding starting material, or protected variation thereof.

It is to be understood that in each illustrative embodiment described herein that includes one or more compounds having chiral centers, all possible diastereomers and enantiomers are described by the structures both collectively as various mixtures, including racemic mixtures, as well as individually as optically active compounds. Where stereochemistry is indicated in illustrative structures, it is to be understood that the indicated stereochemistry is relative and therefore refers only to those selected diastereomers. In addition, in some cases compounds showing relative chemistry refer both the racemic mixtures as well as optically enriched or optically pure enantiomers. As described herein, the preparations, processes, and syntheses for preparing such compounds may he performed using optically enriched or optically pure starting materials, or in the alternative reaction conditions that allow for the asymmetric induction of certain chiral centers.

In another embodiment, compounds of the present invention can he prepared and administered in a wide variety of oral, parenteral and topical dosage forms. Thus, the compounds of the present invention can he administered by injection (e.g. intravenously, intramuscularly, intracutaneously, subcutaneously, intraduodenally, or intraperitoneally). Also, the compounds described herein can be administered by inhalation, for example, intranasally. Additionally, the compounds of the present invention can be administered transdermally. It is also envisioned that multiple routes of administration (e.g., intramuscular, oral, transdermal) can be used to administer the compounds of the invention. Accordingly, the present invention also provides pharmaceutical compositions comprising a pharmaceutically acceptable carrier or excipient and one or more compounds of the invention.

In another embodiment, compounds of the present invention can be prepared and administered in a wide variety of oral, parenteral and topical dosage forms. Thus, the compounds of the present invention can be administered by injection (e.g. intravenously, intramuscularly, intracutaneously, subcutaneously, intraduodenally, or intraperitoneally). Also, the compounds described herein can be administered by inhalation, for example, intranasally. Additionally, the compounds of the present invention can be administered transdermally. It is also envisioned that multiple routes of administration (e.g., intramuscular, oral, transdermal) can be used to administer the compounds of the invention. Accordingly, the present invention also provides pharmaceutical compositions comprising a pharmaceutically acceptable carrier or excipient and one or more compounds of the invention.

For the treatment of HIV, AIDS, and AIDS-related diseases, illustratively the compounds described herein may be formulated in a therapeutically effective amount in conventional dosage forms, including one or more carriers, diluents, and/or excipients. Such formulation compositions may be administered by a wide variety of conventional routes in a wide variety of dosage formats, utilizing art-recognized products. See generally, Remington's Pharmaceutical Sciences, (16th ed. 1980). It is to be understood that the compositions described herein may be prepared from isolated compounds described herein or from salts, solutions, hydrates, solvates, and other forms of the compounds described herein. It is also to be understood that the compositions may be prepared from various amorphous, non-amorphous, partially crystalline, crystalline, and/or other morphological forms of the compounds described herein.

In making the formulations of the compounds described herein, a therapeutically effective amount of the HIV protease inhibitor, in any of the various forms described herein, may be mixed with an excipient, diluted by an excipient, or enclosed within such a carrier which can be in the form of a capsule, sachet, paper, or other container. Excipients may serve as a diluent, and can be solid, semi-solid, or liquid materials, which act as a vehicle, carrier or medium for the active ingredient. Thus, the formulation compositions can be in the form of tablets, pills, powders, lozenges, sachets, cachets, elixirs, suspensions, emulsions, solutions, syrups, aerosols (as a solid or in a liquid medium), ointments, soft and hard gelatin capsules, suppositories, sterile injectable solutions, and sterile packaged powders. The compositions may contain anywhere from about 0.1% to about 99.9% active ingredients, depending upon the selected dose and dosage form. Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions can be formulated so as to provide quick, sustained or delayed release of the active ingredient after administration to the patient by employing procedures known in the art. It is appreciated that the carriers, diluents, and excipients used to prepare the compositions described herein are advantageously GRAS (Generally Regarded as Safe) compounds.

The unitary daily dosage of the compounds described in the invention can vary significantly depending on the host condition, the disease state being treated, the molecular weight of the conjugate, its route of administration and tissue distribution, and the possibility of co-usage of other therapeutic treatments such as radiation therapy. The effective amount to be administered to a patient is based on body surface area, patient weight, and physician assessment of patient condition. An effective dose can range from about 1 ng/kg to about 50 mg/kg, from about 10 ng/kg to about 10 mg/kg, from about 0.10 µg/kg to about 10 mg/kg, from about 1 µg/kg to about 5 mg/kg, and from about 10 µg/kg to about 5 mg/kg.

Any effective regimen for administering the composition comprising a compound of the invention can be used. For example, the composition comprising a compound of the invention can be administered as single doses, or it can be divided and administered as a multiple-dose daily regimen. Further, a staggered regimen, for example, one to three days per week can be used as an alternative to daily treatment, and for the purpose of defining this invention such intermittent or staggered daily regimen is considered to be equivalent to every day treatment and within the scope of this invention.

The compounds described herein may contain one or more chiral centers, or may otherwise be capable of existing as multiple stereoisomers. Accordingly, it is to be understood that the present invention includes pure stereoisomers as well as mixtures of stereoisomers, such as enantiomers, diastereomers, and enantiomerically or diastereomerically enriched mixtures. The compounds described herein may be capable of existing as geometric isomers. Accordingly, it is to be understood that the present invention includes pure geometric isomers or mixtures of geometric isomers.

It is appreciated that the compounds described herein may exist in unsolvated forms as well as solvated forms, including hydrated forms. In general, the solvated forms are equivalent to unsolvated forms and are encompassed within the scope of the present invention. The compounds of the present invention may exist in multiple crystalline or amorphous forms. In general, all physical forms are equivalent for the uses contemplated by the present invention and are intended to be within the scope of the present invention.

Additional features of the present invention will become apparent to those skilled in the art upon consideration of the following description of illustrative embodiments for carrying out the invention.

EXAMPLES

General. All melting points were recorded on a Thomas-Hoover melting point apparatus and are uncorrected. $^1$H NMR and $^{13}$C NMR spectra were recorded on Varian Mercury-Vx-300, Bruker Avance 400, Bruker AV-500, Bruker Avance DRX-500 spectrometers. IR spectra were recorded on a Mattson Genesis II FT-IR spectrometer. Optical rotations were recorded on a Perkin-Elmer 341 or an Autopol III automeric polarimeter. Anhydrous solvents were obtained as follow: THF and diethyl ether by distillation from sodium and benzophenone; pyridine, dichloromethane from $CaH_2$. All other solvents were reagent grade. All moisture sensitive reactions were carried out in a flame dried flask under nitrogen atmosphere. Column chromatography was performed with Whatman 240-400 mesh silica gel under low pressure of 3-5 psi. TLC was carried out with E. Merck silica gel 60-F-254 plates. Ethyl α-N-tosyl iminoacetate was prepared from ethyl glyoxylate and N-toluenesulfonylisocyanate (Sigma-Aldrich) by Weinreb's procedure (Tschaen, D. H.; Turos, E.; Weinreb, S. M. *J. Org. Chem.* 1984, 49, 5058).

Example 1

(±)(R)-Ethyl 2-((R)-tetrahydrofuran-3-yl)-2-(tosylamino) acetate (3). To a mixture of freshly distilled ethyl α-N-tosyl iminoacetate, (1), (255 mg, 1.0 mmol) and 2,3-dihydrofuran (84.2 mg, 1.2 mmol) in dry $CH_2Cl_2$ (6.0 mL) at −78° C. was added a solution of $TiCl_4$ (1.0 M in $CH_2Cl_2$, 1.2 mmol) and the resulting yellow solution containing some precipitate were stirred at −78° C. for an hour. Triethylsilane (581.4 mg, 5.0 mmol) was added to the mixture at −78° C. and the mixture was continuously stirred at −78° C. for 2.0 hours. Saturated sodium bicarbonate solution (15 mL) was used to quench the reaction at −78° C. The mixture was allowed to warm to room temperature and the aqueous layer was extracted with ethyl acetate (3×15 mL). The combined organic extracts were dried over $Na_2SO_4$ and concentrated under reduced pressure. The residue was further purified by flash column chromatography on silica gel to afford the α-N-tosylamino ester (3) (232.7 mg, 71% yield) as a white solid, Mp=104-105° C.; $R_f$=0.29 (40% EtOAc in hexane). $^1$H NMR (500 MHz, $CDCl_3$): δ 1.07 (t, J=7.2 Hz, 3H), 1.84 (m, 1H), 1.97 (m, 1H), 2.41 (s, 3H), 2.49 (m, 1H), 3.64 (m, 1H), 3.72 (m, 2H), 3.78 (m 1H), 3.87 (m, 1H), 3.88 (q, J=7.2 Hz, 2H), 5.22 (d, J=7.0 Hz, 1H), 7.35 (d, J=8.3 Hz, 2H), 7.70 (d, J=8.3 Hz, 2H); $^{13}$C NMR (125 MHz, CDCl$_3$) δ 14.3, 21.9, 28.9, 42.9, 57.4, 62.2, 68.1, 69.7, 127.7, 130.1, 136.9, 144.2, 171.4. IR (film, NaCl), 559.1, 667.8, 816.1, 916.6, 1092.0, 1163.5, 1338.9, 1457.3, 1738.4, 2825.0 cm; $^{-1}$ m/z (ESI) 328.1 (M+H)$^+$.

Example 2

(±) (R)-Ethyl 2-((2R,3R)-2-allyl-tetrahydrofuran-3-yl)-2-(tosylamino)acetate (5a) and (±) (R)-ethyl 2-((2S,3R)-2-allyl-tetrahydrofuran-3-yl)-2-(tosylamino)acetate (6a). To a mixture of freshly distilled α-N-tosyl imino ester 1 (255 mg, 1.0 mmol) and 2,3-dihydrofuran (90.7 mg, 1.2 mmol) in dry CH$_2$Cl$_2$ (6.0 mL) at –78° C. was added a solution of TiCl$_4$ (1.0 M in CH$_2$Cl$_2$, 1.2 mmol) and the resulting yellow solution containing some precipitate were stirred at –78° C. for an hour. Allyltrimethylsilane (229 mg, 2.00 mmol) was added to the mixture at –78° C. and mixture was continuously stirred at –78° C. for 2 hours. Saturated sodium bicarbonate solution (15 mL) was used to quench the reaction at –78° C. The mixture was allowed to warm to room temperature and the aqueous layer was extracted with ethyl acetate (3×15 mL). The combined organic extracts were dried over Na$_2$SO$_4$ and concentrated under reduced pressure. The residue was further purified by flash column chromatography on silica gel to afford the α-N-tosylamino ester 5a (219 mg, 59% yield) and 6a (72.0 mg, 20% yield). Major isomer (±) (R)-ethyl 2-((2R,3R)-2-allyl-tetrahydrofuran-3-yl)-2-(tosylamino)acetate (5a): white crystals, Mp=62-64° C.; R$_f$=0.24 (30% EtOAc in hexane). $^1$H NMR (500 MHz, CDCl$_3$): δ 1.06 (t, J=7.2 Hz, 3H), 1.82 (m, 2H), 2.21 (m, 3H), 2.40 (s, 3H), 3.85-3.72 (m, 4H), 3.90 (q, J=7.2 Hz, 2H), 5.08 (m, 2H), 5.39 (d, J=10.2 Hz, 1H), 5.77 (m, 1H), 7.28 (d, J=8.1 Hz, 2H), 7.69 (d, J=8.1 Hz, 2H); $^{13}$C NMR (75 MHz, CDCl$_3$), δ 13.9, 21.5, 27.7, 38.4, 46.1, 56.0, 61.9, 66.7, 79.0, 117.4, 127.4, 129.7, 134.3, 136.4, 143.9, 170.9; FT-IR (film, NaCl), 668.9, 916.8, 1091.4, 1162.8, 1265.0, 1445.3, 1738.3.2923.2, 2974.2 cm$^{-1}$; m/z (ESI) 390.2 (M$^+$+Na); HRMS (ESI), Calcd for C$_{18}$H$_{25}$NO$_5$S m/z 390.1351 (M+Na)$^+$. found m/z 390.1343 (M+Na)$^+$. Minor isomer (±) (R)-ethyl 2-((2S,3R)-2-allyl-tetrahydrofuran-3-yl)-2-(tosylamino)acetate (6a): wax solid; R$_f$=0.20 (30% EtOAc in hexane); $^1$H NMR (300 MHz, CDCl$_3$) δ 1.12 (t, J=7.2 Hz, 3H), 2.04 (m, 2H), 2.23 (m, 2H), 2.42 (s, 3H), 2.48 (m, 1H), 3.79 (m, 3H), 3.95 (m, 4H), 5.04 (m, 2H), 5.20 (d, J=7.8 Hz, 1H), 5.78 (m, 1H), 7.30 (d, J=8.1 Hz, 2H), 7.73 (d, J=8.1 Hz, 2H); $^{13}$C NMR (75 MHz, CDCl$_3$), δ 13.9, 21.5, 27.4, 33.7, 44.2, 55.7, 61.7, 66.0, 79.6, 117.0, 126.5, 127.4, 129.6, 134.8, 136.1, 143.8, 171.1; FT-IR (film, NaCl), 665.3, 814.7, 1091.2, 1162.5, 1338.3, 1446.2, 1738.3 cm$^{-1}$; m/z (ESI) 366.5 (M–H)$^-$.

Example 3

(±) (R)-Ethyl 2-((2R,3R)-2-cyano-tetrahydrofuran-3-yl)-2-(tosylamino)acetate (5b). To a mixture of freshly distilled α-N-tosyl imino ester (1) (153 mg, 0.60 mmol) and 2,3-dihydrofuran (50.5 mg, 0.72 mmol) in dry CH$_2$Cl$_2$ (4.0 mL) at –78° C. was added a solution of TiCl$_4$ (1.0 M in CH$_2$Cl$_2$, 0.60 mmol) and the resulting yellow solution containing some precipitate were stirred at –78° C. for an hour. Trimethylsilyl cyanide (119 mg, 1.20 mmol) was added to the mixture at –78° C. and mixture was continuously stirred at –78° C. for 0.5 hour. The mixture was allowed to warm to 0° C. and stirred at 0° C. for 5.0 hours. Saturated sodium bicarbonate solution (10 mL) was used to quench the reaction at 0° C. The aqueous layer was extracted with ethyl acetate (3×10 mL). The combined organic extracts were dried over Na$_2$SO$_4$ and concentrated under reduced pressure. The residue was further purified by flash column chromatography on silica gel to afford (5b) (112.3 mg, 64% yield) as a yellow solid, Mp=105-107° C., Rf=0.34 (45% EtOAc in hexane); $^1$H NMR (400 MHz, CDCl$_3$): δ 1.06 (t, J=7.1 Hz, 3H), 1.89 (m, 1H), 2.06 (m, 1H), 2.40 (s, 3H), 2.88 (m, 1H), 4.81-3.81 (m, 5H), 4.70 (d, J=5.7 Hz, 1H), 5.74 (d, J=9.4 Hz, 1H), 7.28 (d, J=8.4 Hz, 2H), 7.70 (d, J=8.4 Hz, 2H); $^{13}$C NMR (100 MHz, CDCl$_3$) δ 13.8 (CH$_3$), 21.5 (CH$_3$), 27.6 (CH$_2$), 48.2 (CH), 55.5 (CH), 62.4 (CH$_2$), 67.9 (CH), 69.0 (CH$_2$), 118.4 (CN), 127.3 (CH), 129.8 (CH), 135.9 (C), 144.3 (C), 169.5 (CO); IR (film, NaCl), 578.2, 666.8, 815.4, 918.5, 1091.6, 1164.0, 1305.1, 1339.5, 1447.8, 1738.6, 2255.6, 2983.1 cm$^{-1}$; m/z (ESI) 375.2 (M$^+$+Na).

Example 4

(±) (S)-Ethyl 2-((S)-tetrahydro-2H-pyran-3-yl)-2-(tosylamino)acetate (8). The procedure described for (3) was used for (8). α-N-tosyl imino ester (1) (255 mg, 1.0 mmol), 3,4-dihydro-2H-pyran (101 mg, 1.20 mmol), TiCl$_4$ (1M in CH$_2$Cl$_2$, 1.20 mmol) and triethylsilane (581.4 mg, 5.00 mmol) to afford (8) (334 mg, 98% yield) as a white solid, Mp=102.2-103.8° C., R$_f$=0.41 (50% EtOAc in hexane); $^1$H NMR (400 MHz, CDCl$_3$): δ 1.06 (3H, t, J=7.1 Hz), 1.41 (ddd, J=23.4, 11.2, 4.1 Hz, 1H), 1.72-1.51 (m, 4H), 1.93 (m, 1H), 2.04 (s, 3H), 3.38-3.32 (m, 2H), 3.92-3.74 (m, 3H), 3.88 (q, J=7.1 Hz, 2H), 7.27 (d, J=8.2 Hz, 2H), 7.69 (d, J=8.2 Hz, 2H); $^{13}$C NMR (100 MHz, CDCl$_3$) δ 13.9, 21.5, 24.6, 25.0, 38.8, 57.1, 61.8, 68.2, 69.8, 127.4, 129.6, 136.3, 143.8, 170.7; IR (film, NaCl) 559.3, 666.8, 1090.0, 1162.9, 1340.1, 1738.5, 2720.9, 2748.1, 2787.0 cm$^{-1}$; m/z (ESI) 342.1 (M+H)$^+$.

Example 5

(±)(S)-Ethyl 2-((2S,3S)-2-allyl-tetrahydro-2H-pyran-3-yl)-2-(tosylamino)acetate (9a) and (±)(S)-ethyl 2-((2R,3S)-2-allyl-tetrahydro-2H-pyran-3-yl)-2-(tosylamino)acetate (10a). The procedure described for (5a) and (6a) was used for (9a) and (10a). α-N-tosyl imino ester (1) (128 mg, 0.50 mmol), 3,4-dihydro-2H-pyran (168 mg, 1.0 mmol), TiCl$_4$ (1M in CH$_2$Cl$_2$, 0.60 mmol) and allyltrimethylsilane (115 mg, 1.00 mmol) to afford unseparable mixture of (9a) and (10a) (178.5 mg, 94% yield) as a white solid, Mp=88-91° C., R$_f$=0.43 (50% EtOAc in hexane); $^1$H NMR (400 MHz, CDCl$_3$): δ 1.00 (t, J=7.1 Hz, 3H, major), 1.07 (t, J=7.1 Hz, 3H, minor), 1.34 (m, 2H), 1.76 (m, 2H), 1.97 (m, 1H), 2.29 (m, 1H), 2.37 (s, 3H), 2.55 (s, 1H), 3.28 (m, 1H, major), 3.43 (m, 1H, major), 3.48 (m, 1H, minor), 3.54 (m, 1H, minor), 3.88 (m, 3H), 4.03 (d, J=8.8 Hz, 1H), 4.97 (m, 2H, minor), 5.08 (m, 2H, major), 5.24 (s, 1H), 5.68 (m, 1H, minor), 5.86 (m, 1H, major), 7.27 (d, J=7.9 Hz, 2H), 7.69 (d, J=7.9 Hz, 2H, major), 7.73 (d, J=7.9 Hz, 2H, minor); $^{13}$C NMR (100 MHz, CDCl3) δ 13.8, 21.5, 23.3, 25.7, 33.2 (minor), 36.7 (major), 39.2 (minor), 41.6 (major), 55.9 (major), 56.7 (minor), 61.5 (minor), 61.8 (major), 65.2 (minor), 67.8 (major), 76.8, 117.0, 127.4, 129.6, 134.5, 136.1 (major), 136.8 (minor), 143.7 (minor), 143.8 (major), 170.5 (major), 171.3 (minor); IR (film, NaCl), 668.0, 815.4, 1089.22, 1163.24, 1340.1, 1738.1, 2931.1 cm$^{-1}$, m/z (ESI) 382.1 (M$^+$+H), 404.2 (M$^+$+Na).

Example 6

(±)(S)-ethyl 2-((2R,3S)-2-cyano-tetrahydro-2H-pyran-3-yl)-2-(tosylamino)acetate (9b) and (±)(S)-ethyl 2-((2S,3S)-2- cyano-tetrahydro-2H-pyran-3-yl)-2-(tosylamino)acetate (10b). The procedure described for 5b was used for 9b and 10b. α-N-tosyl imino ester 1 (153 mg, 0.600 mmol), 3,4-dihydro-2H-pyran (60.6 mg, 0.720 mmol), TiCl$_4$ (1 M in CH$_2$Cl$_2$, 0.720 mmol) and trimethylsilyl cyanide (119 mg, 1.20 mmol) to afford unseparable mixture of 9b and 10b (180.9 mg, 99% yield) as a yellow solid, Mp=107-110° C., R$_f$=0.42 (45% EtOAc in hexane); $^1$H NMR (400 MHz, CDCl$_3$): δ 1.048 (t, J=7.1 Hz, 3H, major), 1.054 (t, J=7.1 Hz, minor), 1.63-1.54 (br, 4H), 2.04 (br, 1H, minor), 2.19 (br, 1H, major), 2.38 (s, 3H), 3.43 (m, 1H, major), 3.70 (m, 1H, minor), 3.99-3.96 (m, 3H), 4.04 (dd, J=9.1, 3.8 Hz, 1H), 4.36 (d, J=9.3 Hz, major), 4.64 (d, J=4.3 Hz), 7.27 (d, J=8.2 Hz, 2H), 7.69 (d, J=8.2 Hz, 2H, minor), 7.72 (d, J=8.2 Hz, 2H, major); $^{13}$C NMR (100 MHz, CDCl$_3$) δ 13.7 (CH$_3$, minor), 13.8 (CH$_3$, minor), 21.5 (CH$_3$), 21.7 (CH$_2$, major), 23.0 (CH$_2$, minor), 23.5 (CH$_2$, major), 24.7 (CH$_2$, minor), 41.4 (CH, minor), 41.6 (CH, major), 55.5 (CH, major), 57.1 (minor), 62.3 (CH$_2$, minor), 62.6 (CH$_2$, major), 64.6 (CH$_2$, minor), 66.7 (CH, minor), 67.5 (CH, major), 67.6 (CH$_2$, major), 115.3 (CN, minor), 117.1 (CN, major), 127.3 (CH, minor), 127.5 (CH, major), 129.7 (CH, minor), 129.8 (CH, major), 135.4 (C, major), 136.3 (C, minor), 169.6 (CO, major), 169.7 (CO, minor); IR (film, NaCl), 548.2, 668.3, 815.3, 919.6, 1021.0, 1089.0, 1164.17, 1341.10, 1447.3, 1735.2, 2255.0, 2339.7, 2360.8, 2866.5, 2935.6 cm$^{-1}$; m/z (ESI) 367.3 (M$^+$+H), 389.2 (M$^+$+Na).

Example 7

(R)-ethyl 2-((3R,5R)-tetrahydro-5-phenylfuran-3-yl)-2-(tosylamino)acetate (13). To a mixture of freshly distilled α-N-tosyl imino ester (1) (76.6 mg, 0.300 mmol) and (R)-2,3-dihydro-2-phenylfuran (11) (52.6 mg, 0.360 mmol) in dry CH$_2$Cl$_2$ (3.0 mL) at −78° C. was added a solution of TiCl$_4$ (1.0 M in CH$_2$Cl$_2$, 0.36 mmol) and the resulting orange solution were stirred at −78° C. for 50 mins. Dry acetonitrile (61.6 mg, 1.50 mmol) was added at −78° C. and the mixture was stirred at −78° C. for 10 mins. Triethylsilane (174.4 mg, 1.50 mmol) was added and the mixture was stirred at −78° C. for an hour. Then the mixture was warmed to −20° C. and stirred at −20° C. for two hours. Then the mixture was retooled to −30° C. and quenched carefully with 10 mL ice-chilled saturated sodium bicarbonate solution. After the mixture was warmed to room temperature, the aqueous layer was extracted with dichloromethane (3×15 mL). The combined organic extracts were dried over Na$_2$SO$_4$ and concentrated under reduced pressure. The residue was further purified by flash column chromatography on silica gel to afford the α-N-tosylamino ester (13) (84.7 mg, 70% yield) as clear crystals, Mp=97-99° C., R$_f$=0.41 (hex:EtOAc=1:1), [α]$^{23}$$_D$=−17.9° (c 1.03, CHCl$_3$); $^1$H NMR (400 MHz, CDCl$_3$): δ 1.06 (t, J=7.3 Hz, 3H), 1.96 (m, 1H), 2.33 (m, 1H), 2.42 (s, 3H), 2.59 (m, 1H), 3.94-3.76 (m, 4H), 4.09 (dd, J=9.1, 7.3 Hz, 1H), 4.99 (t, J=7.0 Hz, 1H), 5.28 (d, J=9.9 Hz, 1H), 7.31 (m, 7I-1), 7.72 (d, J=6.7 Hz, 2H); $^{13}$C NMR (100 MHz, CDCl$_3$) δ 13.9 (CH$_3$), 21.5 (CH$_3$), 36.7 (CH$_2$), 42.3 (CH), 56.7 (CH), 62.0 (CH$_2$), 69.8 (CH$_2$), 79.8 (CH), 125.4 (CH), 127.4 (CH), 128.4 (CH), 129.7 (CH), 136.3 (C), 142.6 (C), 143.9 (C), 170.9 (CO); FT-IR (film, NaCl), 562.1, 666.6, 701.4, 1026.3, 1163.3, 1339.2, 1494.6, 1599.1, 1736.2, 2872.4, 2981.7 cm$^{-1}$; m/z (ESI) 404.1 (M+H)$^+$.

Example 8

(R)-Ethyl 2-((2R,3R,5R)-2-cyano-tetrahydro-5-phenylfuran-3-yl)-2-(tosylamino)acetate (14). To a mixture of freshly distilled α-N-tosyl imino ester (1) (76.6 mg, 0.300 mmol) and (R)-2,3-dihydro-2-phenylfuran (11) (52.6 mg, 0.360 mmol) in dry CH$_2$Cl$_2$ (3.0 mL) at −78° C. was added a solution of TiCl$_4$ (1.0 M in CH$_2$Cl$_2$, 0.36 mmol) and the resulting orange solution were stirred at −78° C. for an hour. Trimethylsilyl cyanide (59.5 mg, 0.60 mmol) was added to the mixture quickly at −78° C. and the mixture was continuously stirred at −78° C. for 0.5 hour. Then the mixture was allowed to warm to −20° C. and stirred at −20° C. for 5.0 hours. Ice-cooled saturated sodium bicarbonate solution (10 mL) was used to quench the reaction carefully at −20° C. The aqueous layer was extracted with dichloromethane (3×10 mL). The combined organic extracts were dried over Na$_2$SO$_4$ and concentrated under reduced pressure. The residue was further purified by flash column chromatography on silica gel to afford (14) (80.4 mg, 65% yield) as a yellow oil, R$_f$=0.28 (hex:EtOAc=1:1), [α]$^{23}$$_D$=−17.2° (c 1.0, CHCl$_3$); $^1$H NMR (400 MHz, CDCl$_3$): δ 1.06 (t, J=7.2 Hz, 3H), 2.09 (m, 1H), 2.43 (s, 3H), 2.45 (m, 1H), 2.92 (m, 1H), 3.95 (m, 3H), 4.82 (d, J=6.4 Hz, 1H), 5.18 (t, J=6.9 Hz, 1H), 5.54 (d, J=9.4 Hz, 1H), 7.30 (m, 7H), 7.74 (d, J=8.2 Hz, 2H); $^{13}$C NMR (100 MHz, CDCl$_3$) δ 13.8 (CH$_3$), 21.6 (CH$_3$), 35.7 (CH$_2$), 47.6 (CH), 55.0 (CH), 62.8 (CH$_2$), 68.3 (CH), 81.8 (CH), 118.1 (CN), 125.4 (CH), 127.4 (CH), 128.0 (CH), 129.9 (CH), 135.6 (C), 140.3 (C), 144.4 (C), 169.6 (CO); FT-IR (film, NaCl), 553.7, 668.4, 815.2, 914.5, 1092.2, 1164.0, 1340.1, 1449.7, 1494.9, 1598.6, 1738.5, 2249.5 cm$^{-1}$; m/z (ESI) 427.4 (M−H)$^-$.

Example 9

(R)-Ethyl 2-((2R,3R,5R)-2-allyl-tetrahydro-5-phenylfuran-3-yl)-2-(tosylamino)acetate (15). To a mixture of freshly distilled α-N-tosyl imino ester (1) (72.2 mg, 0.283 mmol) and (R)-2,3-dihydro-2-phenylfuran (11) (50.0 mg, 0.340 mmol) in dry CH$_2$Cl$_2$ (3.0 mL) at −78° C. was added a solution of TiCl$_4$ (1.0 M in CH$_2$Cl$_2$, 0.36 mmol) and the resulting orange solution were stirred at −78° C. for 50 mins. Dry acetonitrile (58.1 mg, 1.42 mmol) was added at −78° C. and the mixture was stirred at −78° C. for 10 mins. Allyltrimethylsilane (65.2 mg, 0.570 mmol) was added and the mixture was stirred at −78° C. for an hour. Then the mixture was warmed to −20° C. and stirred at −20° C. for two hours. Then the mixture was recooled to −30° C. and the reaction was quenched carefully with 10 mL ice-cooled saturated sodium bicarbonate solution. After the mixture was warmed to room temperature, the aqueous layer was extracted with dichloromethane (3×15 mL). The combined organic extracts were dried over Na$_2$SO$_4$ and concentrated under reduced pressure. The residue was further purified by flash column chromatography on silica gel to afford the α-N-tosylamino ester (15) (89.1 mg, 71% yield) as a yellow oil, R$_f$=0.38 (40% EtOAc in hexane), [α]$^{23}$$_D$=−9.6° (c 1.0, CHCl$_3$); $^1$H NMR (400 MHz, CDCl$_3$): δ 1.05 (t, J=7.1 Hz, 3H), 1.80 (m, 1H), 2.21 (m, 1H), 2.31 (m, 1H), 2.38 (m, 2H), 2.42 (s, 3H), 3.90 (m, 3H), 4.05 (m, 1H), 4.89 (t, J=7.7 Hz, 1H), 5.12 (m, 2H), 5.40 (d, J=9.9 Hz, 1H), 5.89 (m, 1H), 7.33-7.23 (m, 7H), 7.73 (d, J=8.3 Hz, 2H); $^{13}$C NMR (100 MHz, CDCl$_3$) δ 13.8 (CH$_3$), 21.5 (CH$_3$), 36.1 (CH$_2$), 38.6 (CH$_2$), 45.9 (CH), 55.9 (CH), 62.0 (CH$_2$), 79.5 (CH), 79.6 (CH), 117.7 (CH$_2$), 125.7 (CH), 127.4 (CH), 128.3 (CH), 129.7 (CH), 134.1 (C), 136.3 (C), 142.1 (C), 144.0 (C), 171.0 (CO); FT-IR (film, NaCl), 545.1, 667.9, 816.2, 1025.4, 1093.9, 1163.2, 1349.2, 1746.9, 2980.6 cm$^{-1}$; m/z (ESI) 444.1 (M+H)$^+$, 466.3 (M+Na)$^+$.

Example 10

(R)-ethyl 2-((3R,5R)-tetrahydro-5-(naphthalen-2-yl)furan-3-yl)-2-(tosylamino)acetate (16). The procedure described for (13) was used for (16). α-N-tosyl imino ester (1) (76.6 mg, 0.300 mmol), (R)-2,3-dihydro-2-(naphthalen-2-yl)furan (12) (70.3 mg, 0.360 mmol), TiCl$_4$ (1M in CH$_2$Cl$_2$, 0.360 mmol), acetonitrile (61.6 mg, 1.50 mmol) and triethylsilane (174 mg, 1.50 mmol) to afford (16) (89.0 mg, 65% yield) as a yellow oil, R$_f$=0.40 (hex:EtOAc=1:1), [α]$^{23}_D$=−25.2° (c 1.00, CHCl$_3$); $^1$H NMR (500 MHz, CDCl$_3$): δ 1.07 (t, J=7.2 Hz, 3H), 2.04 (m, 1H), 2.40 (m, 1H), 2.41 (s, 3H), 2.64 (m, 1H), 3.87-3.93 (m, 4H), 4.17 (dd, J=9.0, 7.0 Hz, 2H), 5.17 (t, J=7.0 Hz, 1H), 5.31 (d, J=9.5 Hz, 1H), 7.30 (d, J=8.0 Hz, 2H), 7.36 (dd, J=8.5, 1.5 Hz, 1H), 7.46 (m, 2H), 7.74 (d, J=8.0 Hz, 3H), 7.81 (d, J=8.5 Hz, 3H); $^{13}$C NMR (125 MHz, CDCl$_3$) δ 13.9 (CH$_3$), 21.6 (CH$_3$), 36.7 (CH$_2$), 42.4 (CH), 56.8 (CH), 62.0 (CH$_2$), 70.0 (CH$_2$), 80.0 (CH), 123.7 (CH), 123.9 (CH), 125.8 (CH), 126.2 (CH), 127.4 (CH), 127.7 (CH), 127.9 (CH), 128.3 (CH), 129.8 (CH), 132.8 (C), 133.2 (C), 136.4 (C), 140.0 (C), 144.0 (C), 171.0 (CO); FT-IR (film, NaCl) 550.9, 593.0, 675.2, 737.1, 817.5, 1029.7, 1091.7, 1161.9, 1349.3, 1599.0, 1743.8 cm$^{-1}$; m/z (ESI) 454.1 (M+H)$^+$.

Example 11

(R)-ethyl 2-((2S,3R,5R)-2-cyano-tetrahydro-5-(naphthalen-2-yl)furan-3-yl)-2-(tosylamino)acetate (17). The procedure described for (5b) was used for (17). α-N-tosyl imino ester (1) (76.6 mg, 0.300 mmol), (R)-2,3-dihydro-2-(naphthalen-2-yl)furan (12) (70.3 mg, 0.360 mmol), TiCl$_4$ (1M in CH$_2$Cl$_2$, 0.36 mmol) and trimethylsilyl cyanide (89.3 mg, 0.900 mmol) to afford (17) (84.7 mg, 59% yield) as a yellow oil, R$_f$=0.40 (hex: EtOAc=1:1), [α]$^{23}_D$=−55.2° (c 1.05, CHCl$_3$); $^1$H NMR (400 MHz, CDCl$_3$): δ 1.05 (t, J=7.1 Hz, 3H), 2.19 (m, 1H), 2.41 (s, 3H), 2.52 (m, 1H), 2.97 (m, 1H), 3.97 (m, 3H), 4.90 (d, J=6.5 Hz, 1H), 5.35 (t, J=6.9 Hz, 1H), 5.70 (d, J=5.3 Hz, 1H), 7.31 (d, J=8.2 Hz, 2H), 7.39 (dd, J=8.6, 1.6 Hz, 1H), 7.48 (m, 2H), 7.76 (d, J=8.2 Hz, 2H), 7.82 (m, 4H); $^{13}$C NMR (100 MHz, CDCl$_3$) δ 13.8 (CH$_3$), 21.6 (CH$_3$), 35.6 (CH$_2$), 47.5 (CH), 55.0 (CH), 62.8 (CH$_2$), 68.4 (CH), 82.0 (CH), 118.2 (CN), 123.2 (CH), 124.4 (CH), 126.2 (CH), 126.4 (CH), 127.4 (CH), 127.7 (CH), 128.1 (CH), 128.6 (CH), 129.9 (CH), 133.0 (C), 135.7 (C), 137.6 (C), 144.4 (C), 169.6 (CO); FT-IR (film, NaCl), 667.6, 817.2, 1092.0, 1163.7, 1446.5, 1738.2, 2820.8, 2922.3 cm$^{-1}$; m/z (ESI) 477.5 (M Example 12

(R)-ethyl 2-((2R,3R,5R)-2-allyl-tetrahydro-5-(naphthalen-2-yl)furan-3-yl)-2-(tosylamino)acetate (18). The procedure described for (15) was used for (18). α-N-tosyl imino ester (1) (76.6 mg, 0.300 mmol), (R)-2,3-dihydro-2-(naphthalen-2-yl)furan (12) (70.6 mg, 0.360 mmol), TiCl$_4$ (1M in CH$_2$Cl$_2$, 0.36 mmol), acetonitrile (61.6 mg, 1.50 mmol) and allyltrimethylsilane (68.6 mg, 0.600 mmol) to afford (18) (104.8 mg, 71% yield) colorless oil, R$_f$=0.48 (Hex: EtOAc=3:2), [α]$^{23}_D$=−17.0° (c 0.73, CHCl$_3$); $^1$H NMR (500 MHz, CDCl$_3$): δ 1.06 (t, J=7.0 Hz, 3H), 1.87 (m, 1H), 2.29-2.39 (m, 2H), 2.42 (s, 3H), 2.48 (m, 2H), 3.87-3.97 (m, 3H), 4.13 (q, J=6.0 Hz, 1H), 5.07 (t, J=7.5 Hz, 1H), 5.14-5.21 (m, 2H), 5.41 (d, J=10.0 Hz, 1H), 5.92-5.98 (m, 1H), 7.31 (d, J=8.5 Hz, 2H), 7.40 (dd, J=8.5, 1.5 Hz, 1H), 7.46 (m, 2H), 7.74-7.82 (m, 6H); $^{13}$C NMR (125 MHz, CDCl$_3$) δ 13.9 (CH$_3$), 21.6 (CH$_3$), 36.0 (CH$_2$), 38.7 (CH$_2$), 46.0 (CH), 56.0 (CH), 62.0 (CH$_2$), 79.6 (CH), 79.9 (CH), 117.8 (CH$_2$), 123.9 (CH), 124.4 (CH), 125.8 (CH), 126.1 (CH), 127.5 (CH), 127.7 (CH), 128.0 (CH), 128.2 (CH), 129.8 (CH), 132.9 (C), 133.2 (C), 134.2 (CH), 136.3 (C), 139.6 (C), 144.0 (C), 171.0 (CO); FT-IR (film, NaCl) 499.4, 666.2, 815.7, 1024.4, 1161.81, 1348.4, 1744.2 cm$^{-1}$; m/z (ESI) 494.1 (M+H)$^+$, 516.2 (M+Na)$^+$.

Example 13

Deprotection of tosyl group from 5a. (5a) (84.8 mg, 0.231 mmol) was mixed with 1N LiOH (3.23 mL, 3.23 mmol) and THF (1.15 mL) and was stirred at room temperature for an hour. Then the solution was adjusted to pH=2 with 1N HCl. The aqueous layer was extracted with ethyl acetate (3×15 mL). The combined organic extracts were dried over anhydrous Na$_2$SO$_4$ and the solvent was removed in vacuum. The crude product was used for the next reaction without purification. Thus, to a flask equipped with a condenser were added the crude product from last step, sodium phosphate dibasic (179.4 mg, 1.26 mmol), methanol (5.0 mL) and 3% Na/Hg (2.95 g, 3.83 mmol). The mixture was refluxed for one day. Then sodium phosphate dibasic (179.4 mg, 1.26 mmol) and 3% Na/Hg (2.95 g, 3.83 mmol) were added. The mixture was refluxed for another day. Water (2.0 ml) was used to quench the reaction. Mercury was removed and washed with methanol. The solution was concentrated. The resulting solid was dissolved in 10 mL methanol and sodium phosphate dibasic was removed by filtration. After removing the solvent from the filtrate, the crude product was further purified by column chromatography on silica gel (eluent:CHCl$_3$:CH$_3$OH:aqueous ammonia=5:3:1) to afford the desired product (7a) (41.8 mg, 98% yield, two steps) as a white solid, R$_f$=0.36 (CHCl$_3$: CH$_3$OH:aqueous ammonia=5:3:1). NMR (500 MHz, CD$_3$OD): δ 1.86 (ddd, J 15.0, 12.5, 7.5 Hz, 1H), 2.08 (m, 1H), 2.25 (dt, J=14.5, 7.5 Hz, 1H), 2.40 (m, 1H), 2.45 (in, 1H), 3.54 (d, J=6.0 Hz), 3.81 (m, 2H), 3.97 (dt, J=11.0, 3.5 Hz, 1H), 5.06 (dt, J=10.5, 1.0 Hz, 1H), 5.13 (dd, J=15.5, 2.0 Hz, 1H), 5.86 (m, 1H); $^{13}$C NMR (125 MHz, CD$_3$OD), δ 28.0 (CH$_2$), 38.2 (CH$_2$), 44.6 (CH), 56.5 (CH), 66.0 (CH$_2$), 79.7 (CH), 116.5 (CH$_2$), 134.4 (CH), 171.9 (CO); FT-IR (film, NaCl), 575.4, 687.1, 1365.1, 1404.1, 1512.8, 1639.3 cm$^{-1}$; HRMS (ESI), Calcd for C$_9$H$_{15}$NO$_3$: m/z 186.1130 (M+H)$^+$. found m/z 186.1127 (M+H)$^+$.

Example 14

Determination of Diastereomeric Ratios. The chiral products (13)-(18) was reduced to primary alcohol with LiAlH$_4$ in ethyl ether at 0° C., then the crude product was coupled with (R)-Mosher acid using EDCI and DMAP. The coupling product was purified by flash chromatography and the $^{19}$F NMR spectra of the desired Mosher ester was taken to determine the de % with integration (Lee, J.; Kobayashi, Y.; Tezuka, K.; and Kishi Y. *Org. Lett.*, 1999, 1, 2181-84).

TABLE 1

Inhibition of HIV Protease by compounds of the following formula

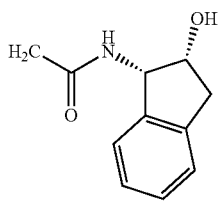

| No. | R¹ | R² | R³ | Y | $K_i$ (nM) |
|---|---|---|---|---|---|
| 1 | 1-naphthyl | allyl | H | p-MePhSO$_2$ | 0.70 |
| 2 | Ph | H | H | p-MePhSO$_2$ | 0.75 |
| 3 | 1-naphthyl | H | H | p-MePhSO$_2$ | 0.72 |
| 4 | Ph | H | isoBu | p-MeOPhSO$_2$ | >1000 |
| 5 | PhCH$_2$ | ally | H | p-MePhSO$_2$ | 0.41 |
| 6 | PhCH$_2$ | H | H | p-MePhSO$_2$ | 0.28 |
| 7 | PhCH$_2$ | H | isoBu | p-MePhSO$_2$ | 19 |
| 8 | m-MeOPh | H | H | p-MePhSO$_2$ | >1000 |
| 9 | 1-naphthyl | allyl | H | p-MeOPhSO$_2$ | 51 |
| 10 | PhCH$_2$ | H | H | p-MeOPhSO$_2$ | 1.4 |
| 11 | p-MeOPhCH$_2$ | H | H | p-MePhSO$_2$ | >10 |
| 12 | p-MeOPhCH$_2$ | allyl | H | p-MePhSO$_2$ | 84 |
| 13 | PhCH$_2$ | H | H | p-MePhSO$_2$ | 200 |
| 14 | p-HOCH$_2$PhCH$_2$ | H | H | p-MePhSO$_2$ | 480 |
| 15 | p-HOCH$_2$PhCH$_2$ | allyl | H | p-MePhSO$_2$ | 370 |
| 16 | PhCH$_2$ | H | H | p-HOCH$_2$PhSO$_2$ | >1000 |
| 17 | Ph | allyl | H | benzamide | >1000 |
| 18 | Ph | allyl | H | p-FPhSO$_2$ | >1000 |
| 19 | Ph | 2-N-benzylaminoethyl | H | p-MePhSO$_2$ | 3 |
| 20 | Ph | 2-HO-2-Ph-ethyl single isomer | H | p-MePhSO$_2$ | 670 |
| 21 | Ph | 2-HO-2-Ph-ethyl diastereomeric mixture | H | p-MePhSO$_2$ | 4 |
| 22 | Ph | 2,3-dihydroxypropyl | H | p-MePhSO$_2$ | 27 |
| 23 | Ph | 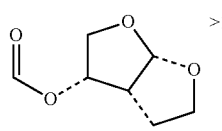 | H | p-MePhSO$_2$ | >1000 |
| 24 | Ph | (same indanyl acetamide structure) | H | p-MePhSO$_2$ | 500 |
| 25 | Ph | allyl | H | p-MePhSO$_2$ | >1000 |
| 26 | 2-naphthyl | 2-HO-2-Ph-ethyl single isomer, lower Rf | H | p-MePhSO$_2$ | 150 |
| 27 | 2-naphthyl | 2-HO-2-Ph-ethyl single isomer, higher Rf | H | p-MePhSO$_2$ | 480 |
| 28 | Ph | allyl | H | (bicyclic furanofuran formate) | >1000 |
| 29 | Ph | 2-OH-3-N-morpholino-propyl | H | p-MePhSO$_2$ | >1000 |
| 30 | Ph | N-benzylaminomethyl | H | p-MePhSO$_2$ | >1000 |

TABLE 1-continued

Inhibition of HIV Protease by compounds of the following formula

[Structure: tetrahydrofuran ring with R¹ at 5-position, R² at 2-position, CH(CO₂H)(NR³)(Y) substituent at 3-position]

| No. | R¹ | R² | R³ | Y | $K_i$ (nM) |
|---|---|---|---|---|---|
| 31 | Ph | [cis-1-formamido-2-hydroxyindane] | H | p-MePhSO₂ | >1000 |
| 32 | Ph | [trans-1-formamido-2-hydroxyindane] | H | p-MePhSO₂ | 500 |
| 33 | Ph | 1-E-propenyl | H | p-MePhSO₂ | >1000 |
| 34 | 2-naphthyl | allyl | H | p-MePhSO₂ | 1000 |
| 35 | p-methoxymethyl-Ph | allyl | H | p-MePhSO₂ | >1000 |

TABLE 2

Inhibition of HIV Protease

| No. | Compound | $K_i$ (nM) |
|---|---|---|
| 1 | [Pyrrolidine with naphthyl, tosyl sulfonyl, CO₂H, and hydroxy-allyl substituents] | 95 |
| 2 | [Methoxy-benzenesulfonamide linked to bicyclic ether with OMe group, COOH] | >1000 |
| 3 | [Methylenedioxy-fused bicyclic ether with CH(CO₂H)(NHTs) substituent] | 32 |

What is claimed is:

1. A pharmaceutical composition comprising compound of the formula:

[Structure: tetrahydrofuran with R⁵, R⁸ substituents on ring; R⁷ substituent; side chain bearing CH(CO₂R¹¹)(NR²SO₂R¹)]

Wherein:
R¹ is optionally substituted alkyl or aryl;
R² is hydrogen or optionally substituted alkyl;

$R^5$ is hydrogen, optionally substituted alkyl, optionally substituted alkenyl, or nitrile;
$R^7$ is hydrogen;
$R^8$ is optionally substituted arylalkyl; and
$R^{11}$ is hydrogen, alkyl, arylalkyl, or a pro-drug moiety; and one or more carriers, diluents or excipients, and combinations thereof.

2. The pharmaceutical composition of claim 1, wherein $R^1$ is optionally substituted aryl.

3. The pharmaceutical composition of claim 2, wherein the aryl is phenyl.

4. The pharmaceutical composition of claim 2, wherein the aryl is substituted with alkyl, alkoxy, nitro, amino, or alkoxyalkyl.

5. The pharmaceutical composition of claim 1, wherein $R^8$ is aryl optionally substituted with hydroxyl, alkoxy or hydroxyalkyl.

6. The pharmaceutical composition of claim 1, wherein $R^5$ is arylalkyl, alkoxyalkyl, or aminoalkyl.

7. A method for treating a patient in need of relief from HIV, AIDS, or an AIDS-related disease, the method comprising the step of administering to the patient a therapeutically effective amount of the pharmaceutical composition of claim 1.

* * * * *